(12) United States Patent
Han et al.

(10) Patent No.: US 8,030,538 B2
(45) Date of Patent: Oct. 4, 2011

(54) CATTLE BETA-CASEIN GENE TARGETING VECTOR USING HOMOLOGOUS RECOMBINATION

(75) Inventors: Yong-Mahn Han, Daejeon (KR); Kyung-Kwang Lee, Daejeon (KR); Mira Chang, Gyeongsangbuk-Do (KR); Deog-Bon Koo, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 575 days.

(21) Appl. No.: 10/574,747

(22) PCT Filed: Nov. 18, 2005

(86) PCT No.: PCT/KR2005/003923
§ 371 (c)(1),
(2), (4) Date: Sep. 17, 2008

(87) PCT Pub. No.: WO2006/057499
PCT Pub. Date: Jun. 1, 2006

(65) Prior Publication Data
US 2009/0013419 A1    Jan. 8, 2009

(30) Foreign Application Priority Data

Nov. 23, 2004 (WO) ................ PCT/KR2004/003034

(51) Int. Cl.
C12P 21/00 (2006.01)
A01K 67/027 (2006.01)
C12N 15/00 (2006.01)
C12N 5/00 (2006.01)

(52) U.S. Cl. ......... 800/7; 435/320.1; 435/462; 435/463; 435/325; 800/15; 800/24

(58) Field of Classification Search .................. None
See application file for complete search history.

(56) References Cited

U.S. PATENT DOCUMENTS

| 5,741,957 | A | 4/1998 | Deboer et al. ........... 800/2 |
| 5,843,705 | A * | 12/1998 | DiTullio et al. ........... 800/7 |
| 6,180,761 | B1 | 1/2001 | Han et al. ........... 530/360 |
| 6,713,662 | B1 | 3/2004 | Karatzas et al. ........... 800/14 |
| 2003/0024002 | A1 | 1/2003 | Colman et al. ........... 800/21 |
| 2004/0168208 | A2 | 8/2004 | Karatzas et al. ........... 800/7 |
| 2005/0177878 | A1 * | 8/2005 | Melo et al. ........... 800/7 |

FOREIGN PATENT DOCUMENTS

| KR | 2003-0060772 A | 7/2003 |
| KR | 2004-0045528 A | 6/2004 |
| WO | WO 2006/057499 A1 | 6/2006 |

OTHER PUBLICATIONS

Pennisi et al. Hard Clones. Science, 2000, vol. 288, pp. 1722-1727.*

Bonsing et al. Complete Nucleotide Sequence of the Bovine Beta-Casein Gene, Austrailian Journal of Biological Sciences, 1988, vol. 41(4), pp. 527-537.*

Shen et al. The ht-PAm cDNA Knock-In the Goat Beta-Casein Gene Locus, Chinese Journal, of Biotechnology, May 2004, vol. 20(3), pp. 361-365.*

Ulrike Müller, "*Ten years of gene targeting: targeted mouse mutants, from vector design to phenotype analysis*", Mechanisms of Development 82, Jan. 21, 1999, pp. 3-21.

Sohn, et al., "*High level expression of the bioactive human interleukin-10 in milk of transgenic mice*", Journal of Biotechnology 103, Jan. 6, 2003, pp. 11-19.

Baguisi, et al., "*Production of goats by somatic cell nuclear transfer*", Nature Biotechnology, vol. 17, May, 1999, pp. 456-461.

Kim, et al., "*High-level expression of human lactoferrin in milk of transgenic mice using genomic lactoferring sequence*", Japanese Biochemical Society, 126, Mar. 19, 1999, pp. 320-325.

McCreath, "*Production of gene-targeted sheep by nuclear transfer from cultured somatic cells*", Nature, vol. 405, Jul. 29, 2000, pp. 1066-1069.

Van Berkel, "*Large scale production of recombinant human lactoferrin in the milk of transgenic cows*", Nature Biotechnology, vol. 20, May 2002, pp. 484-487.

Clark, A. John, "*The mammary gland as a bioreactor: expression, processing, and production of recombinant proteins*", Journal of Mammary Gland Biology and Neoplasia, vol. 3, No. 3, 1998, pp. 337-350.

Brophy, et al., "*Cloned transgenic cattle produced milk with higher levels of β-casein and $\kappa_1$-casein* ", Nature Biotechnology, Feb. 2003, vol. 21, pp. 157-162.

Schnieke, et al., "*Human factor IX transgenic sheep produced by transfer of nuclei from transfected fetal fibroblasts*"; Science, vol. 278, Dec. 19, 1997, pp. 2130-2133.

* cited by examiner

*Primary Examiner* — Deborah Crouch
(74) *Attorney, Agent, or Firm* — Ohlandt, Greeley, Ruggiero & Perle, L.L.P.

(57) ABSTRACT

The present invention relates to a bovine beta-casein gene targeting vector comprising (1) a first region having a length of 5 to 12 kb which is homologous to the promoter and its flanking nucleic acid sequences of bovine beta-casein gene, and comprising exon 1, intron 1, and exon 2 of bovine beta-casein gene; (2) a region for cloning a nucleic acid coding for desired proteins; (3) a region for coding a positive selection marker; (4) a second region having a length of 2.8 to 3.5 kb which is homologous to the nucleic acid sequences of bovine beta-casein gene, and comprising exon 5, 6, 7 and 8, and intron 5, 6 and 7 of bovine beta-casein gene; wherein the nucleic acid segment corresponding to the first region is located upstream to the nucleic acid segment corresponding to the second region in the 5'-3' arrangement of beta-casein gene. The present invention also relates to method producing the transgenic cattle which is bovine beta-casein gene-targeted with a gene coding a desired protein using the said vector and obtaining a large scale of a desired protein from the milk of the said transgenic cattle.

9 Claims, 21 Drawing Sheets pBluescript II SK (+)

enzymes which do not cut the beta-casein gene locus in BC10 vector
Sma I , BamH I , Sal I , Spe I , Cla I

CATTLE BETA-CASEIN GENE TARGETING VECTOR USING HOMOLOGOUS RECOMBINATION

TECHNICAL FIELD

The present invention relates to bovine beta-casein gene targeting vectors that function through homologous recombination, bovine somatic cells that are gene-targeted with the said vectors and embryos that are nuclear-transferred with the said bovine somatic cells. The present invention also relates to methods for producing amounts of desired proteins from the milk of the transgenic cattle that are prepared by implanting the said embryos.

BACKGROUND ART

Our continuous efforts in animal genomics to identify genes and their functions have made it possible to generate transgenic animals. Transgenic animals have been created great commercial value in industries such as biomedicine and agriculture. Various techniques such as microinjection, viral transfection, sperm vector, application of embryonic stem (ES) cells and somatic cell nuclear transfer (SNCT) have also been developed to prepare transgenic animals or so called genetically-modified animals.

The microinjection method, which injects a DNA molecule into the male or female pronucleus of fertilized eggs (Harbers et al., Nature., 293(5833); 540-2, 1981; Brinster et al., Cell., 27; 223-231, 1981; Gordon et al., Proc Natl Acad Sci USA., 77(12); 7380-7384; Costantini et al., Nature., 294(5836); 92-94), has been widely employed to produce transgenic animals (Hammer et al., Nature., 315(6021); 680-683, 1985; van Berkel et al., Nat. Biotechnol., 20(5); 484-487, 2002; Damak et al., Biotechnology (NY), 14(2); 185-186, 1996). However, the efficiency of this technique in the production of transgenic animals is very low in that only 2-3% of the injected eggs give rise to transgenic offspring (Clark et al., Transgenic Res., 9; 263-275, 2000). The production of transgenic animals using the microinjection method is also a labor-intensive and costly procedure requiring large numbers of animals and facilities (Brink et al., Theriogenology, 53; 139-148, 2000). Another disadvantage of this technique is that it cannot control the integration sites and the copy numbers of the inserted genes. The resulting random integration sometimes leads to a low or nonspecific expression of the transgenes. It was further reported that the unregulated expression of certain transgenes sometimes cause lethality in the embryonic development (Wei et al., Annu Rev Pharmacol Toxicol., 37; 119-141, 1997).

The retrovirus-mediated method is also widely used in order to genetically manipulate animals (Soriano et al., Genes Dev., 1(4); 366-375, 1987; Hirata et al., Cloning Stem Cells., 6(1); 31-36, 2004). Under this technique, the desired gene sequences are introduced into the animal genomes by using virus-mediated vectors. Although viral transformation is more efficient than pronuclear injection, random insertion of the foreign genes and mosaicism are entailed due to multiple integrations (Piedrahita et al., Theriogenology, 53(1); 105-116, 2000). Additionally, the maximum size of the introduced genes is usually limited to approximately 7 kb and there is concerning of the potential interference caused by virally encoded proteins (Wei et al., Annu Rev Pharmacol Toxicol., 37; 119-141, 1997; Yanez et al., Gene Ther., 5(2); 149-159, 1998).

To circumvent the problems referred to above, a gene targeting technique that can insert or remove a DNA segment at a specific location was developed. The gene targeting technique was first applied to the mouse embryonic stem cells to study gene function. Mouse embryonic stem cells are now being used to introduce predetermined genetic modifications into embryos. A number of specific gene-targeted mice have been produced through the manipulation of mouse embryonic stem cells using the technique(Brandon et al., Curr Biol., 5(6); 625-634, 1995; Capecchi et al., Science, 244(4910); 1288-1292, 1989; Thompson et al., Cell, 56(2); 313-321, 1989; Hamanaka et al., Hum Mol. Genet., 9(3); 353-361, 2000; Thomas et al, Cell, 51(3); 503-512, 1987; te Riele et al., Proc. Natl. Acad Sci USA, 89(11); 5182-5132, 1992; Mansour et al., Nature, 336(6197), 348-352, 1988; Luo et al., Oncogene, 20(3); 320-328, 2001). The extension of this gene targeting method to other mammalian species, particularly livestock, could bring numerous biomedical benefits such as mass production of pharmaceutical proteins and animal disease models.

Until now, most recombinant therapeutic proteins have been produced by cell culture systems, which use cells such as yeast, bacteria or animal cells. However, it is difficult to produce proteins in large scale using cell culture systems because of the limited capacity and high cost. Furthermore, for some proteins, additional steps are required to introduce proper posttranslational modifications such as glycosylation, γ-carboxylation, hydroxylation and so on (Houdebine et al., Transgenic Res., 9(4-5); 305-320, 2000; Lubo et al., Transgenic Res., 9(4-5); 301-304, 2000).

Animal bioreactors that produce valuable or therapeutic proteins have been evaluated as efficient and cost-effective expression systems. In particular, the large-scale production of therapeutic recombinant proteins from transgenic animals is much more cost-effective compared to the cell culture system (van Berkel et al., Nat. Biotechnol., 20(5); 484-487, 2002). Recombinant proteins produced in animal milk were known to be post-translationally modified in a way very similar to the human counterpart proteins (Edmunds et al., Blood, 91(12); 4561-4571, 1998; Velander et al., Proc Natl Acad Sci USA., 89(24); 12003-12007, 1992; van Berkel et al, Nat. Biotechnol., 20(5); 484-487, 2002).

Cow's milk is composed of approximately 88% water, 3.3% protein and the remaining carbohydrates and fat. The caseins, comprising 80% milk protein, are divided into four groups, alpha S1, alpha S2, beta and kappa casein. Beta casein is the most abundant protein in milk and is expressed in a concentration of 10 mg/ml in bovine milk (Brophy et al., Nat. Biotechnology., 21(2); 157-162, 2003).

The somatic cell nuclear transfer (SCNT) technique is more efficient way to make transgenic animals compared to the microinjection method because almost all of the cloned animals derived from transformed somatic cells are transgenic. animals (Brink et al., Theriogenology, 53; 139-148, 2000). It is also possible to predetermine the sex of animals and create a genetically homogeneous herd in order to produce a uniform product (Lubo et al., Transgenic Res., 9(4-5); 301-304, 2000; van Berkel et al., Nat. Biotechnol., 20(5); 484-487, 2002).

Until now, ES cells and vector constructs for targeting a specific gene have been considered as prerequisite elements to generate gene-targeted animals. However, there is a limitation in the use of ES cells from large livestocks, although some studies have developed ES-like cells in pig and cattle (Doetschman et al., Dev Biol., 127(1); 224-227, 1988; Stice et al., Biol Reprod., 54(1); 100-110, 1996; Sukoyan et al., Mol Reprod Dev., 36(2); 148-158, 1993; Iannaccone et al., Dev Biol., 163(1); 288-292, 1994; Pain et al., Development, 122(8); 2339-2348, 1996; Thomson et al., Proc Natl Acad Sci USA., 92(17); 7844-7848, 1995; Wheeler et al., Reprod Fertil Dev., 6(5); 563-568, 1994).

Instead, the use of normal somatic cells as nuclear donor cells has been suggested as an efficient and practical method to produce transgenic cattle (Brophy et al., Nat. Biotechnol., 21(2); 157-162, 2003; Cibelli et al., Science, 280(5367); 1256-1258, 1998; Campbell et al., Nature, 380(6569); 64-66, 1996; Wilmut et al., Experientia, 47(9); 905-912, 1997; Denning et al., Cloning stem cells, 3(4); 221-231, 2001), suggesting the possibility that somatic cells instead of embryonic stem cells can be used for targeting specific genes.

With the application of SCNT technique, promoter regions of milk protein genes have been used to direct the expression of recombinant protein in the milk of transgenic large animals (Schnieke et al. Science, 278(5346); 2130-2133, 1997; Baguisi et al., Nat. Biotechnol., 17(5); 456-461, 1999; Brophy et al., Nat. Biotechnol., 21(2); 157-162, 2003). However, the use of this technique in farm animals is still not practical unless the problems of low expression and/or ectopic expression due to the random insertion of genes are solved. The ectopic expression of foreign protein causes early embryonic lethality and is particularly severe in nervous system, as most nervous system structures develop in late embryonic and early postnatal stages (Gao et al., Neurochem Res., 24(9); 1181-1188, 1999). To eliminate or reduce these side-effects, a new method that allows the foreign protein to be expressed only during the lactation period and strictly in the mammary gland have been invented (Houdebine et al., Transgenic Res., 9(4-5); 305-320, 2000). Gene-targeting, known as the introduction of site-specific modification into a genome by homologous recombination event, is a powerful tool for tissue-specific expression of recombinant proteins (Muller et al., Mech Dev., 82(1-2); 3-21, 1999; Clark et al., J Mammary Gland Biol Neoplasia., 3(3); 337-350, 1998).

The generation of a first knock-in ovine has opened the door to make it possible to produce therapeutic foreign protein-targeted large animals (McCreath et al., Nature, 405 (6790); 1066-1069, 2000). The COLT-2 targeting vector which has homology regions for COL1A1 gene that is highly expressed in fibroblasts was developed, allowing the promoter-trap enrichment of gene-targeting events. AATC2 transgene comprised of human al-antitrypsin (AAT) complementary DNA within an ovine beta-lactoglobulin (BLG) expression vector was designed to direct expression in the mammary gland, having separate transcription unit. The amount of AAT secreted from targeted lambs was 37-fold more than that from the sheep with multiple and random integration of the genes (McCreath et al., Nature, 405(6790); 1066-1069, 2000). Thus, gene targeting is now regarded to be the most powerful method to produce large amount of therapeutic protein. However, the application of the promoter-trap targeting vector is limited to transcriptionally active genes in the somatic cells. In general, transcriptionally active genes are more amendable to gene targeting than silent genes because they have a higher frequency of homologous recombination (Kuroiwa et al., Nat. Genet., 36(7); 775-780, 2004).

Milk proteins are expressed in a tissue-specific manner in the mammary gland. An over-expression of foreign protein is possible without causing lethality in embryonic or post-natal development by manipulating a gene coding of the milk proteins. Among such proteins, beta-casein would be one of the best candidates since it is expressed abundantly. The bovine beta-casein exists as a single copy gene in total genome and is not known to be expressed in the somatic cells except for those in the mammary gland. The targeting of foreign genes into the beta-casein gene, which is not expressed in the normal somatic cells, cannot be carried out by vectors utilizing the promoter trap.

Based on this background, the present inventors have created targeting vector cassettes specific for the bovine beta-casein gene, vectors inserted with a foreign gene using the said cassettes, bovine somatic cell introduced with the said vector, and nuclear-transferred embryo with the said bovine cell. The present inventors found that the foreign gene was correctly targeted to the beta-casein gene of bovine genomic DNA and confirmed the targeting events with the said vector were highly efficient. Therefore, the present inventors have been completed transgenic cattle which could produce a large scale of desired therapeutic protein using the said bovine beta-casein gene targeting vector cassette.

SUMMARY OF THE INVENTION

It is an object of the present invention to provide a bovine beta-casein gene targeting vector comprising (1) a first region having a length of 5 to 12 kb which is homologous to the promoter and its flanking nucleic acid sequences of bovine beta-casein gene, and comprising exon 1, intron 1, and exon 2 of bovine beta-casein gene; (2) a region for cloning a nucleic acid coding for desired proteins; (3) a region for coding a positive selection marker; (4) a second region having a length of 2.8 to 3.5 kb which is homologous to the nucleic acid sequences of bovine beta-casein gene, and comprising exon 5, 6, 7 and 8, and intron 5, 6 and 7 of bovine beta-casein gene; wherein the nucleic acid segment corresponding to the first region is located upstream to the nucleic acid segment corresponding to the second region in the 5'-3' arrangement of beta-casein gene.

It is another object of the present invention to provide a bovine somatic cell which is bovine beta-casein gene-targeted with the said targeting vector.

It is another object of the present invention to provide an embryo which is nuclear-transferred with the said somatic cell.

It is another object of the present invention to provide a method for preparing bovine beta-casein gene-targeted somatic cell, which comprises the steps of (1) introducing the above vector into a bovine somatic cell; (2) occurring homologous recombination events in the bovine somatic cell; and (3) selecting the bovine beta-casein gene-targeted somatic cell.

It is another object of the present invention to provide a method for preparing transgenic cattle, which comprises the steps of (1) introducing the above vector into a bovine somatic cell; (2) occurring homologous recombination events in the bovine somatic cell; (3) selecting the bovine beta-casein gene-targeted somatic cell; (4) introducing the above gene-targeted cell into a nuclear-removed bovine oocyte to produce nuclear-transferred embryo; and (5) implanting the above embryo into a surrogate to produce cloned transgenic cattle.

It is yet another object of the present invention to provide a method for preparing a large scale of desired therapeutic proteins from milk of cloned cattle produced using the above method.

DETAILED DESCRIPTION OF THE INVENTION

Figure 1:
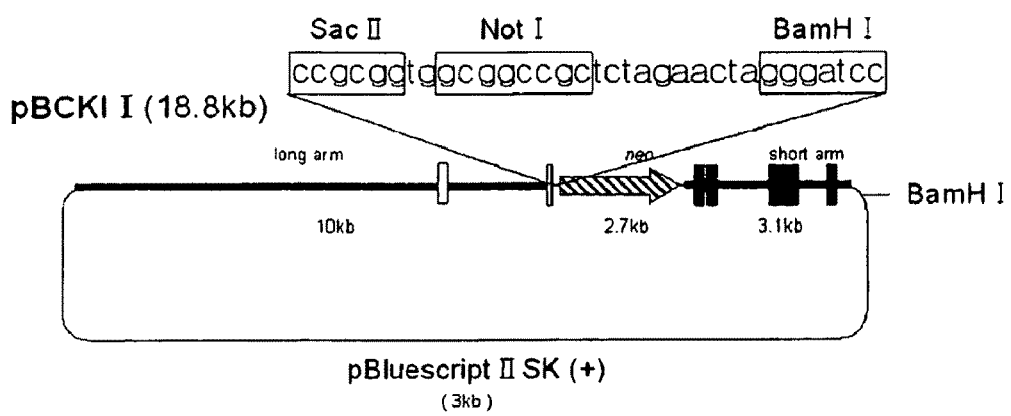
FIG. 1 depicts 18.8 kb pBCKI I vector cassette targeting the bovine beta-casein gene, derived from a pBluescript II SK(+) plasmid. The vector also includes Sac II, Not I, and BamH I restriction sites in front of neo gene and BamH I site at the back of short arm region.

The present invention relates to preparing bovine beta-casein gene targeting vectors used to generate beta-casein gene-targeted cattle which produce amounts of desired therapeutic proteins from milk. Whereas goat and sheep produce milk to 300 and 200 liters, respectively, a year, cattle produce milk up to 6,300 liter a year. Cattle are optimal species that could be used as animal bioreactors, however, there has been no report about targeting the desired gene to milk protein genes in bovine. The present invention relates to vector constructs which can target to a bovine beta-casein gene of bovine milk protein genes and a method preparing beta-casein gene targeted cattle which produce amounts of therapeutic proteins using the vector constructs of the present invention.

In an aspect, the present invention relates to a bovine beta-casein gene targeting vector comprising (1) a first region having a length of 5 to 12 kb which is homologous to the promoter and its flanking nucleic acid sequences of bovine beta-casein gene, and comprising exon 1, intron 1, and exon 2 of bovine beta-casein gene; (2) a region for cloning a nucleic acid coding for desired proteins; (3) a region for coding a positive selection marker; (4) a second region having a length of 2.8 to 3.5 kb which is homologous to the nucleic acid sequences of bovine beta-casein gene, and comprising exon 5, 6, 7 and 8, and intron 5, 6 and 7 of bovine beta-casein gene; wherein the nucleic acid segment corresponding to the first region is located upstream to the nucleic acid segment corresponding to the second region in the 5'-3' arrangement of beta-casein gene.

The term "gene targeting vector", as used herein, means a vector that can remove or insert a desired gene to a specific-genomic locus and includes a nucleic acid sequence homologous to a particular gene for homologous recombination. A gene targeting vector of the present invention is a beta-casein targeting vector which inserts nucleic acid sequences coding desired proteins to beta-casein gene in genome in the 5'-3' arrangement. The terms, vectors and vector cassettes are used herewith interchangeably, and the vectors can be either circular or linear form. The gene-targeting vectors of the present invention are bovine beta-casein gene-targeting vectors.

The beta-casein targeting vector of the present invention comprises a first region and a second region that are homologous to the sequences of the beta-casein gene that are located before and after the cloning site. A first region corresponds to the long arm and a second region corresponds to the short arm.

Among components of the invented bovine beta-casein gene targeting vectors, particularly, "a first region" and "a second region" are important parameters to determine the gene targeting efficiency.

"A first region" of herein, is characterized by having a length of 5 to 12 kb which has a DNA sequences homologous to the promoter and its flanking sequences of bovine beta-casein gene, and comprising exon 1-2 and intron 1 of bovine beta-casein gene. A bovine beta-casein gene promoter has been known to be a good promoter to induce high expression of a foreign protein (Kim et al., J Biochem (Tokyo)., 126(2); 320-325, 1999) and is a good candidate to express a large scale of desired foreign proteins. Preferably, 5.5 kb to 10 kb is preferable as a length.

"A second region" of herein, characterized by having a length of 2.8 to 3.5 kb which is homologous to a DNA sequence of bovine beta-casein gene, and comprising exon 5-8 and intron 5-7 of bovine beta-casein gene. 3.0 kb to 3.2 kb is preferable as a length.

The first region is located upstream to the second region in the 5'-3' arrangement of beta-casein gene.

The term "homology", as used herein, means the degree of similarity between nucleic acid sequences of the first region or a second region and the endogenous beta-casein gene sequences corresponding to these first and second regions. The sequences are homologous to each other when the sequences exhibit at least 90%, preferably at least 95% sequence identity.

The term "(multiple) cloning site", as used herein, means a nucleic acid sequence comprising at least two distinct nucleotide sequence specifically recognized and digested by restriction enzymes to permit insertion of nucleic acid sequence coding desired proteins.

A desired protein, which can inserted to the MCS on a vector of the present invention, may includes all proteins having medical or industrial application, such as hormones, cytokines, enzymes, coagulation factors, carrier proteins, receptors, regulatory proteins, structural proteins, transcription factors, antibodies, antigens, etc.

Specific examples of the desired proteins include, but not limited to, thrombopoietin, human growth hormone, growth hormone releasing hormone, growth hormone releasing peptide, interferons, interferon receptors, colony-stimulating factor, glucagon-like peptides, G-protein-coupled receptor, interleukins, interleukin receptors, enzymes, interleukin binding proteins, cytokine binding proteins, macrophage activating factor, macrophage peptide, B cell factor, T cell factor, protein A, suppressive factor of allergy, cell necrosis glycoprotein, immunotoxin, lymphotoxin, tumor necrosis factor, tumor inhibitory factor, transforming growth factor, alpha-1 antitrypsin, albumin, alpha-lactalbimin, apolipoprotein-E, erythroprotein, hyper-glycosylated erythroprotein, angiopoietins, hemoglobin, thrombin, thrombin receptor activating peptide, thrombomodulin, factor VII, factor VIIa, factor VIII, factor IX, factor XIII, plasminogen activator, fibrin binding protein, urokinase, streptokinase, hirudin, protein C, C-reactive protein, renin inhibitor, collagenase inhibitor, superoxide dismutase, leptin, platelet derived growth hormone, epithelial growth factor, epidermal growth factor, angiostatin, angiotensin, osteogenic growth factor, osteogenesis stimulating protein, calcitonin, insulin, atriopeptin, cartilage inducing factor, elcatonin, connective tissue activator protein, tissue factor pathway inhibitor, follicle stimulating hormone, luteinizing hormone, FSH releasing hormone, nerve growth hormone, parathyroid hormone, relaxin, secretin, somatomedin, insulin-like growth factor, adrenocorticotrophic hormone, glucagon, cholecystokinin, pancreatic polypeptide, gastrin releasing peptide, corticotropin releasing factor, thyroid stimulating hormone, autotaxin, lactoferrin, myostatin, receptor, receptor antagonist, cell surface antigen, virus-derived vaccine antigen, monoclonal antibody, polyclonal antibody, and so on.

The term "selection marker", as used herein, is required for selecting transformed cell with the vector. The selection marker gene confers resistances to drugs, nutritional requirement and cytotoxic drugs, or induces selectable phenotype such as fluorescence and a color deposit. There is a positive selection marker and a negative selection marker. "Positive selection marker" makes cell expressing positive selection markers to survive against selective agent, so that be capable of conferring positive selection characteristic for the cell expressing that marker. The positive selection marker includes, but not limited to, neomycin, hygromycin, histidinol dehydrogenase, guanine phosphosribosyltransferase, and so on.

The vector of the present invention comprises negative selection marker as additional component. "Negative selection marker" removes cells with random-integration, so that be capable of conferring negative selection characteristic for the cell expressing that marker. The negative selection marker includes, but not limited to, thymidine kinase (tk), hypoxanthine phosphoribosyl transferase (Hprt), cytosine deaminase, diphtheria toxin (DT), and so on. The negative selection marker locates at the 5' terminus of a first DNA sequence or the 3' terminus of the second DNA sequence. Among those negative selection markers, tk and DT is used generally. In the present invention, DT gene was utilized as a negative selection marker. Whereas tk requires treatment of gancyclovir, DT does not require any other treatments. It is also reported that tk-carrying cells treated with gancyclovir show potent 'bystander effect' on co-culturing with unmodified cells and gancyclovir suppress the growth of cells (Yoshiyasu Kaneko et al., Cancer Letters, 96; 105-110, 1995). In those aspects, DT is more preferable than tk.

The positive and negative selection markers of the present invention have independent promoter and polyA regions. The promoter includes, but not limited to, simian virus 40 (SV40) promoter, mouse mammary tumor virus (MMTV) promoter, human immunodeficiency virus-long terminal repeat (HIV-LTR) promoter, moloney virus promoter, cytomegalovirus (CMV) promoter, epstein-barr virus (FBV) promoter, respiratory syncytial virus (RSV) promoter, RNA polymerase II promoter, β-actin promoter, human hemoglobin promoter, human muscle creatin promoter, and so on.

The nucleic acid coding the desired protein is integrated to a beta-casein gene locus of cellular genomic DNA in host cell by homologous recombination, and is expressed in the cell instead of the endogenous beta-casein protein.

To improve efficiency of homologous recombination events, the bovine beta-casein gene targeting vectors of the present invention have characteristics as follows.

The efficiency of gene integration of the nucleic acid coding a desired protein into a beta-casein gene locus of cellular genomic DNA has been shown to have relation with the targeting vector system, especially with the degree of similarity and length of nucleic acid sequences of homologous regions (Scheerer et al., Mol Cell Biol., 14(10)6663-6673, 1994; Thomas et al., Cell, 51(3); 503-512, 1987; Hasty et al., Mol Cell Biol., 11(11); 5586-5591, 1991; Lu et al., Blood, 102(4); 1531-1533, 2003). The present invention maximized the efficiency by optimizing the position and length of homologous region of the first and second regions. In addition, to minimize positional interference when homologous recombination events occurs, the positive selection markers of the invented vectors were inserted into loci corresponding exon 3-4 and intron 2-4 regions of bovine beta-casein gene. In addition, in the present invention, multiple cloning sites (MCS) were developed in the behind of "a first region" to insert foreign protein genes for ease. In addition, final vector scheme of the present invention comprising gene coding desired gene for gene targeting is different from the one of previous (SHEN Wei et al., Chinese Journal of Biotechnology, 20(3); 361-365, 2004). 3 of homology regions for homologous recombination events existed in vector of the previous report, because gene coding desired protein were inserted randomly into a first region of the vector (SHEN Wei et al., Chinese Journal of Biotechnology, 20(3); 361-365, 2004). Whereas, only two homology regions for recombination event existed in vector of the present invention, because gene coding desired protein were inserted into MCS of vector. Accordingly, when the vector cassette of the present invention is used, construction of the vector for gene targeting is simple and targeting efficiency of vector is much higher than that of previous one (SHEN Wei et al., Chinese Journal of Biotechnology, 20(3); 361-365, 2004).

Indeed, the present vector system induced homologous recombination events even in the somatic cells that are transcriptionally silent, leading to the stable integration of the foreign protein gene into a beta-casein gene locus.

Figure 2:
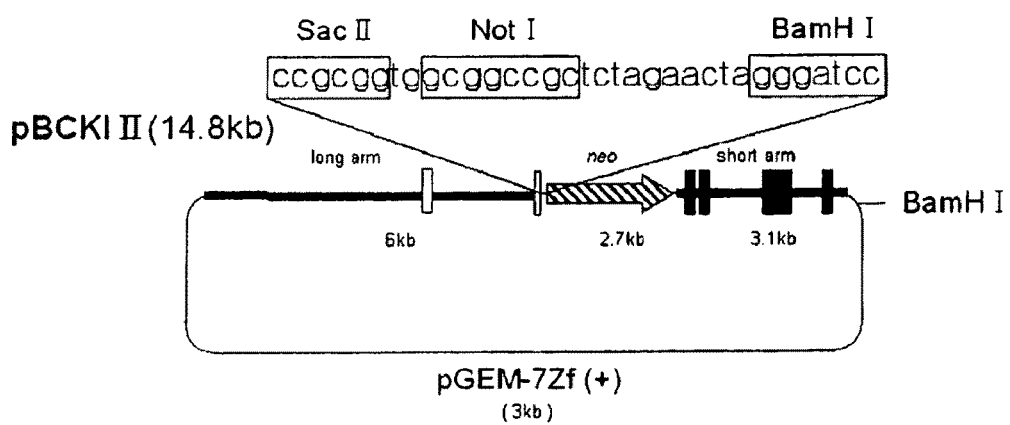
FIG. 2 depicts 14.8 kb pBCKI II vector cassette targeting the bovine beta-casein gene, derived from a pGEM-7Zf(+) plasmid (Promega).

In a preferred embodiment of this invention, pBCKI I and pBCKI II vectors, and pBCKIDT I and pBCKIDT II vectors harboring a negative selection marker were prepared as targeting vectors.

pBCKI I vector, about 18.8 kb in length, was derived from pBluescript II SK(+) plasmid. The first region of pBCKI I vector is about 10 kb in length and it includes 8 kb sequences harboring bovine beta-casein promoter, exon 1, intron 1 and exon 2 of the bovine beta-casein gene. A second region of pBCKI I vector is about 3.1 kb in length and it includes exons 5-8, introns 5-7 and a portion of intron 4 and 8 as shown in FIG. 2. The pBCKI I vector includes a neo gene as a selection marker, SV40 early promoter and polyA sequences. The pBCKI I vector includes three restriction enzymes sites (Sac II, Not I and BamH I), for the insertion of nucleic acid coding desired proteins as shown in FIG. 1.

pBCK II vector, about 14.8 kb in length, was derived from pGEM7Zf(+) plasmid. The first region of pBCKI II is about 6 kb in length and it includes bovine beta-casein promoter having a length of about 4 kb and axon 1, intron 1 and exon 2 of the bovine beta-casein. A second region of pBCKI II vector is about 3.1 kb in length and includes exons 5-8, introns 4-7 and a portion of intron 4 and 8 as shown in FIG. 2. The pBCKI II vector includes a neo gene as a selection marker gene, SV40 early promoter and polyA. The pBCKI II vector includes three restriction enzymes sites (Sac II, Not I and BamH I), for the insertion of nucleic acid coding desired proteins as shown in FIG. 2.

The pBCKIDT I and pBCKIDT II vectors were developed as inserting DT gene into Xho I and Sal I sites of the pBCKI I and pBCKI II vectors.

The targeting vectors according the present invention can be prepared using general DNA recombination techniques. Site-specific cleavage and ligation can be accomplished by using the enzymes known to the art.

Figure 17:
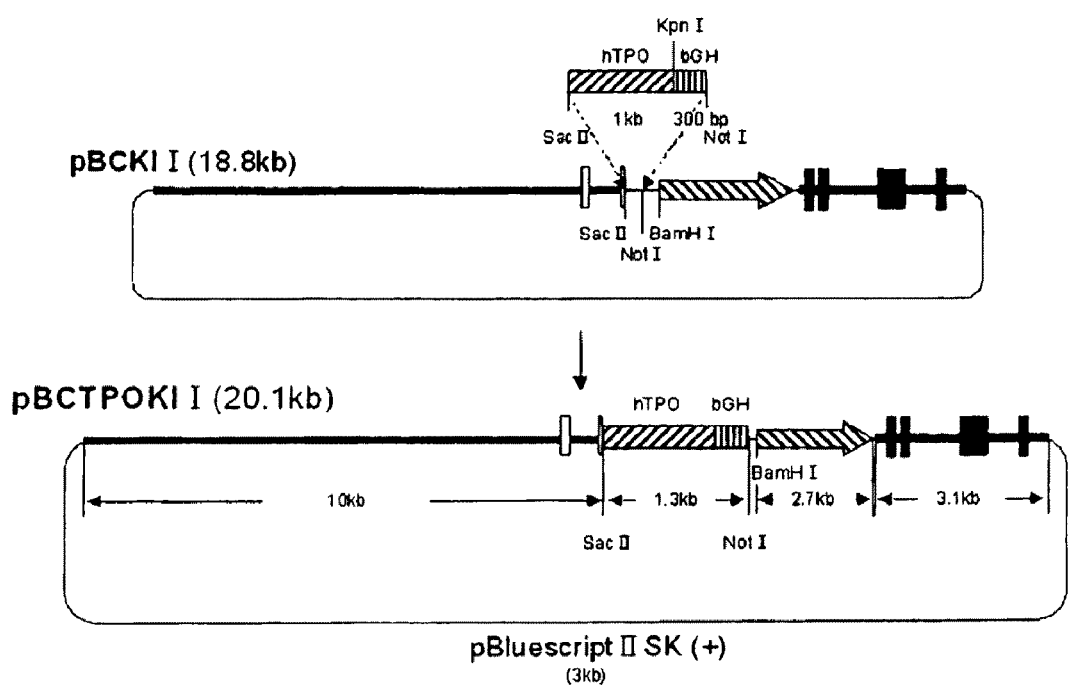
FIG. 17 shows introduction of a valuable gene into the pBCKI I vector. As an example of the genes for therapeutic proteins, human thrombopoietin (hTPO) cDNA was inserted into the invented PBCKI I vector cassettes. The 1.0 kb of the hTPO cDNA coding for the full length form was amplified by PCR in our previous study, and the poly(A) additional signal sequence of the bovine growth hormone (bGH) gene, which is 300 bp in length, was ligated into the Kpn I site to downstream of the hTPO cDNA fragment (Sohn, DNA Cell Biol., 18(11); 845-852, 1999). The 1.3 kb DNA fragment including hTPO cDNA and bGH gene was inserted into Sac II and Not I sites of the pBCKI I vectors, generating the 20.1 kb pBCTPOKI I vector construct.
Figure 18:
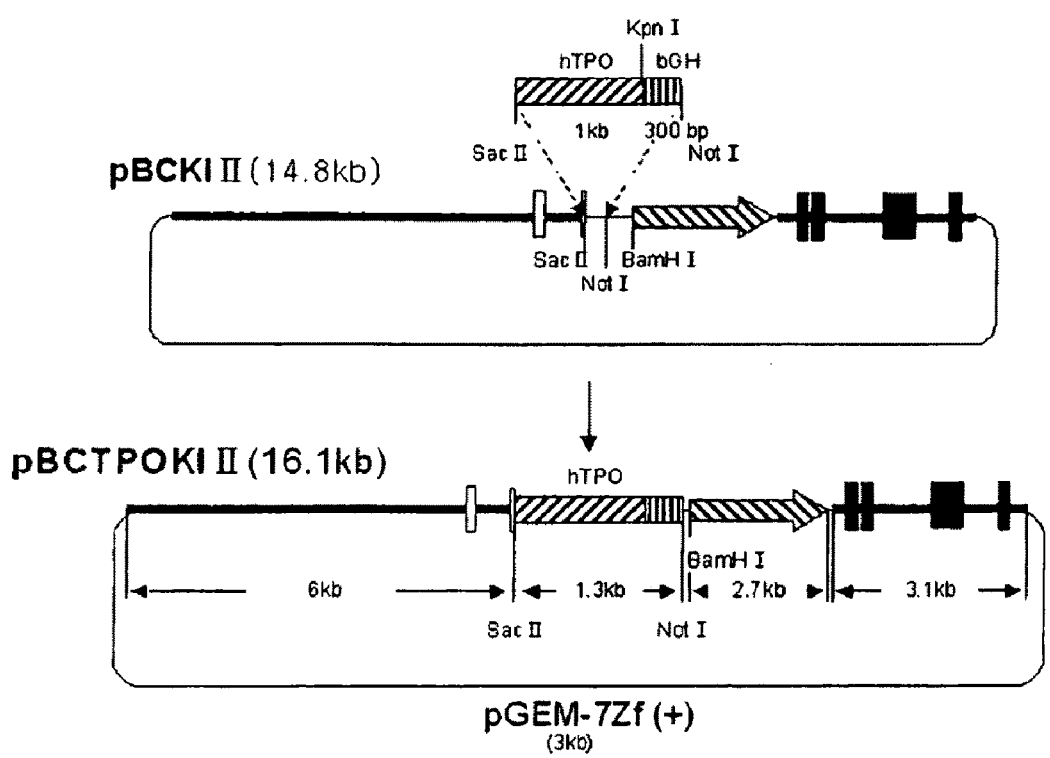
FIG. 18 shows introduction of the hTPO cDNA into pBCKI II vector cassette. The resultant 16.1 kb pBCTPOKI II construct was generated and the procedures were the same as described in FIG. 17.
Figure 19:
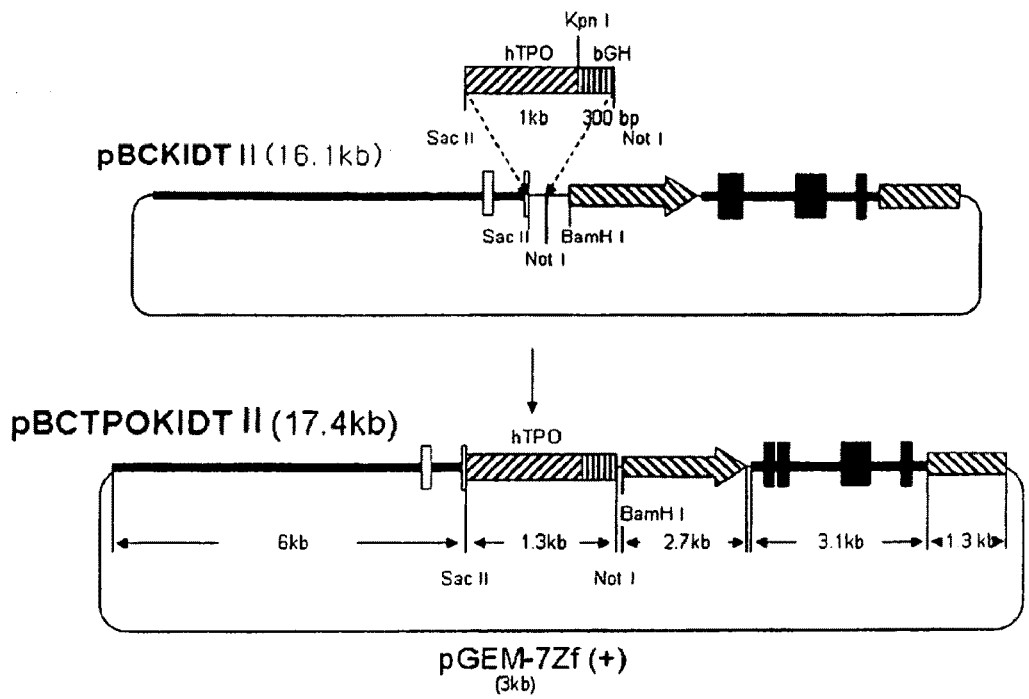
FIG. 19 shows introduction of the hTPO cDNA into pBCKIDT II vector cassette. As a result, 17.4 kb pBCTPOK-IDT II construct was generated and the construction procedures were the same as described in FIG. 17.

In a specific embodiment, human thrombopoietin (TPO) gene was inserted into BCKI I and BCKI II (FIGS. 17, 18 and 19). The 1 kb human TPO cDNA fragment flanked by 0.3 kb fragment of bovine growth hormone (bGH) gene was constructed (Sohn et al., DNA Cell Biol., 18(11); 845-852, 1999). The bGH gene was inserted to encode s stable messenger RNA.

Human thrombopoietin is one of the major hemopoietic regulators participating in series of megakaryocytopoiesis, that is, proliferation and differentiation of megakaryocytes inducing production of platelets. As a primary physiological regulator of platelet production, it plays a pivotal role in promoting the proliferation and maturation of megakaryocytes. Severe neutropenia and thrombocytopenia are seen in patients undergoing aggressive chemotherapy and bone marrow transplantation for hematologic malignancies and solid tumors (Lok et al., Stem Cells, 12(6); 586-598, 1994; Kaushansky et al., Stem Cells, 15(1); 97-102, 102-103, 1997; Kaushansky et al., Ann Intern Med., 126(9); 731-733, 1997; Kaushansky et al., Leukemia, 11(3); 426-427, 1997; Kaushansky et al., Annu Rev Med., 48; 1-11, 1997). It was confirmed that recombinant TPO has ability to ameliorate thrombocytopenia in animal models so that showed the potential use for therapeutic purpose. The safety and efficacy of TPO was approved in Phase I clinical trials (Fanucchi et al., N Engl J. Med., 336(6); 404-409, 1997; Basser et al., Lancet., 348 (9037); 1279-1281, 1996; O'Malley et al., Blood, 88(9); 3288-3298, 1996). It also appears that TPO could be used to enhance the recovery of platelet production in myelosuppressed patients undergoing cancer chemotherapy.

Particularly, *Escherichia coli* cells transformed with the pBCTPOKIDT II vectors were deposited with the international depositary authority as KCTC 10864BP at Korea collection for type cultures (KCTC, #52 Oun-dong Yuseong-gu, Daejeon, South Korea) on 17 Oct. 2005.

Among the above two vectors, the pBCKI II vectors harboring the first region having a length of 6 kb are more efficient than pBCKI I vectors in targeting to the beta-casein gene in genome. And, pBCKIDT II vectors harboring negative selection marker, DT gene, showed 4 to 5-fold higher targeting efficiency than pBCKI II vectors. In the present invention, 36.6% bEF and 41.4% bESF cells were targeted with the pBCKITPOKIDT II vectors, and the targeting efficiency was 3.3-fold higher (41.4%/12.7%) than the that of previous targeting vectors, 12.7% in goat fetal fibroblasts (SHEN Wei et al., Chinese Journal of Biotechnology, 20(3); 361-365, 2004). Therefore, we confirmed that the vectors of the present invention are highly efficient bovine beta-casein gene targeting vectors.

In another aspect, the present invention relates to bovine somatic cell which is gene-targeted with the above vectors.

A cell targeted with a vector of the present invention is derived from eukaryotes, and can be primary, secondary, or permanent cells. Preferably, the cells are derived from cattle, sheep, goats, pigs, horses, rabbits, dogs, monkeys, and so on, but not limited to. Useful tissues capable of detaching or activating cells are, but not limited to, livers, kidneys, spleens, bones, marrows, thymuses, hearts, muscles, lungs, brains, seminal glands, ovaries, islets, intestines, ears, skins, pancreatic tissues, prostate glands, bladders, embryos, immune systems, hematopoiesis systems, and so on. And cell types are, but not limited to, fibroblasts, epithelial cells, nerve cells, embryonic cells, liver cells, ovarian follicle cells, and so on.

A transfection method of the vector includes any method of introducing a nucleic acid into the cell, and the transfection can be carried out using an appropriate technique well known in this art. The transfection methods include, but not limited to, electroporation, calcium phosphate co-precipitation, retroviral infection, microinjection, DEAE-dextran, cationic liposome transfections and so on. When transfection, a linear form of vectors, which is digested with a restriction enzymes, is more preferable than a circular form vectors, is exemplary.

In particular, a beta-casein targeting-vector inserted with a human thrombopoietin (hTPO) was introduced into bovine embryonic fibroblasts (bEF) and bovine ear skin fibroblasts (bESF) using Lipofectamine™ 2000 reagent (Invitrogen). Cationic liposome interacts efficiently with negative charged DNA and the DNA-liposome complexes are associated with the cell membrane, thereby leading to DNA internationalization. Insertion of the gene-targeting vector into a specific gene was detected and confirmed by a long range PCR and a southern blot assay from the colonies survived after the treatment with antibiotics. Using the procedures, clones derived from bESF cells targeted with hTPO at the beta-casein gene were obtained. The number 81 cell clone was designated as BCTPOKIbESF81 and deposited with the Korean Collection for Type Cultures (KCTC) located in #52, Oun-dong, Yusong-ku, Taejon 305-333, Republic of Korea on Nov. 10, 2004, under the accession number KCTC-10720BP.

In another aspect, the present invention relates to embryo which is nuclear-transferred with the said bovine somatic cell.

The term, "Nuclear transfer" is a process that genetic material of the nuclear donor cells is transferred into the enucleated oocytes. The nuclear transfer technique makes it possible to produce genetically identical animal clones because genetic material of the same donor cell is transferred into the recipient cytoplast.

In another aspect, the present invention relates to a method for producing a bovine beta-casein gene-targeted somatic cell, which comprises the steps of (1) introducing the bovine beta-casein gene targeting vector into a bovine somatic cells; (2) occurring homologous events in the transfected somatic cell; and (3) selecting the bovine beta-casein gene-targeted somatic cell.

The bovine beta-casein gene targeting vectors of the present invention, more particularly, pBCKI I, pBCKI II, pBCKIDT I, and pBCKIDT II were optimized to improve targeting efficiency. Accordingly, production efficiency of the bovine somatic cell which is bovine beta-casein gene-targeted with a gene coding a desired protein can be improved by using the above vector.

In addition, the vector in the step (1) is introduced into cells in form of linearized or deleted form lacking plasmid vector backbone.

In another aspect, the present invention relates to a method to provide a method for preparing cloned transgenic cattle, which comprises the steps of (1) introducing the above vector into a bovine somatic cell; (2) occurring homologous recombination events in the bovine somatic cell; (3) selecting the bovine beta-casein gene-targeted somatic cell with a desired gene by homologous recombination; (4) introducing the above gene-targeted cell into nuclear-removed bovine oocyte to produce nuclear-transferred embryo; and (5) implanting the above embryo into surrogates to produce cloned transgenic cattle.

As referred above, the invention is proper to produce cloned gene-targeted cattle wherein the invented vectors are optimized for bovine beta-casein gene-targeting.

To remove the genetic materials of the oocytes, various methods such as physical enucleation, chemical treatment and centrifugation with Cytochalasin B treatment are employed (Tatham et al., Hum Reprod., 11(7); 1499-1503, 1996). In this invention, the physical enucleation method using a glass micropipette was used.

A gene-targeted somatic cell is introduced into a nuclear-removed animal embryo by using the techniques such as cell fusion method and intracytoplasmic cell injection (ICCI), etc. The cell fusion method is simple and useful for large production of embryos. The ICCI method permits maximum exposure of a nucleus isolated from donor cells to the cytosol in recipient cytoplasts.

The fusion of somatic cell and enucleated oocyte is accomplished by changing charges on cell surface by electric pulse. It is convenient to use an electro-cell manipulator that the pulse length and voltage are easily controllable.

In another aspect, the present invention relates to a method for producing a desired protein from milk, which comprises the steps of introducing the vector according to the present invention into an animal somatic cell; selecting the cell targeted with a desired gene by homologous recombination; introducing the gene-targeted cell into a nuclear-removed animal embryo; implanting the embryo into a milk-producing animal to produce a transgenic animal; and producing milk from the transgenic animal.

The nuclear-transferred embryos are activated and developed in vitro to the blastocyst stage and then and then implanted to recipients.

The activation of cloned embryo induces reinitiation of cell cycle, which is temporarily quiescent, whereby the cleavage of embryo is possible. To activate a cloned embryo, the activation of cell cycle arrest factors, such as maturation-promoting factor (MPF), mitogen-activated protein (MAP) kinase, and so on, should be suppressed, wherein for the suppression of the activation, the increase of intracellular calcium ion in a cloned embryo is necessary. The activation of cell can be accomplished by the dramatic increase of calcium influx induced by electro-stimulation or chemical treatment such as ionomycin, 6-dimethylaminopurine (6-DMAP), and so on, wherein the above methods can be used independently or together. In the present invention, the reconstructed embryos were treated with ionomycine+6-DMAP and developed in vitro to a blastocyst stage.

As a result, cloned offspring which can express desired proteins during lactation period are generated. Using the transgenic animals produced by the targeting vector systems of the present invention, desired proteins can be obtained in large quantity from the milk without causing severe lethality during the embryonic or post-natal development.

In another aspect, the present invention relates to a method to obtain desired protein from milk of the cloned transgenic cattle produced using above method.

The desired proteins expressed in milk can be purified using conventional methods such as salting out (examples: ammonium sulfate precipitation; sodium phosphate precipitation), solvent precipitation (example: protein fraction precipitation using acetone, ethanol and so on), dialysis, gel filtration, ion exchange, column chromatography such as reverse column chromatography, ultra filtration, combinations thereof, and so on (Maniatis et al., Molecular Cloning: A Laboratory Manual, Cold Spring Harbor Laboratory, Cold Spring Harbor, N.Y.(1982); Sambrook et al., Molecular Cloning: A Laboratory Manual, 2d Ed., Cold Spring Harbor Laboratory Press(1989); Deutscher, M., Guide to Protein Purification Methods Enzymology, vol. 182. Academic Press. Inc., San Diego, Calif. (1990))

Hereinafter, the present invention will be described in detail referring to the following examples. However, the examples according to the present invention can be modified in other forms, and the scope of the present invention is not limited to the following examples.

EXAMPLE 1

Bovine Gene Targeting Vector Construction 1-1 pBCKI I and pBCKI II Vector Construction In this invention, we employed a bovine beta-casein gene promoter locus which direct expression of foreign therapeutic genes in the milk.

Figure 9:
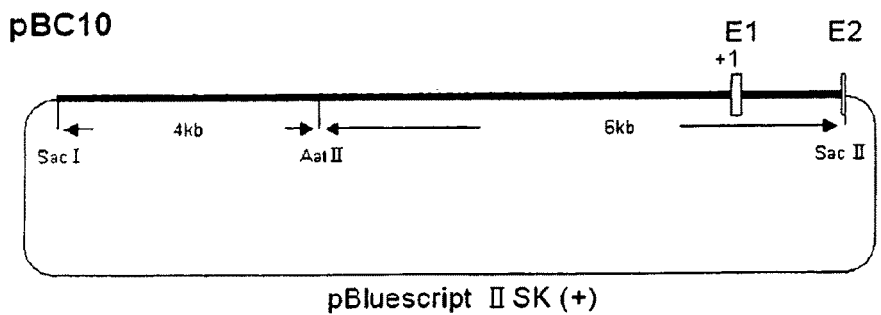
FIG. 9 shows the pBC10 vector constructed in our previous study (Kim et al., J Biochem (Tokyo)., 126(2); 320-5, 1999). The pBC10 vector is based on a pBluescript II SK vector backbone and includes the bovine beta-casein promoter region, which is 10 kb in length. The promoter region contains 8 kb of the 5'-flanking sequence of gene, the untranslated exon 1 and 2 (vertical open boxes), and 2 kb of intron 1 of bovine beta-casein gene. The promoter has restriction enzyme sites for Sac I, Aat II, and Sac II, but there is no recognition sequences of other restriction enzymes such as Sma I, BamH I, Sal I, Spe I and Cla I.
Figure 10:
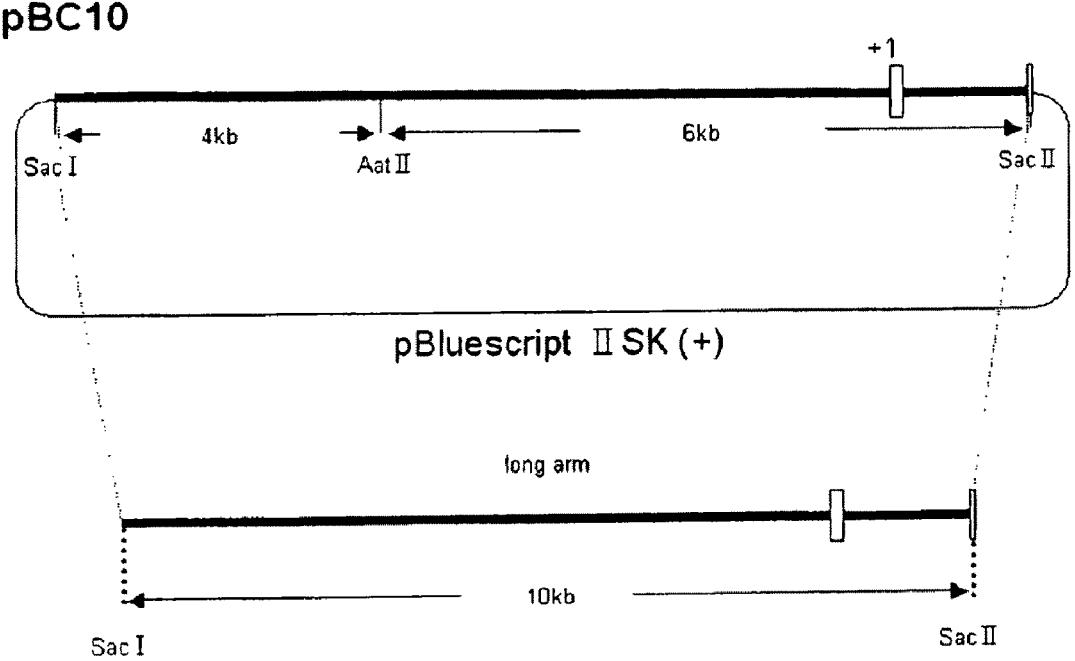
FIG. 10 shows the isolated 10 kb DNA fragment from the pBC10 vector digested with Sac I and Sac II restriction enzymes. The isolated 10 kb DNA fragment is used for a long arm of the pBCKI I vector cassette.
Figure 11:
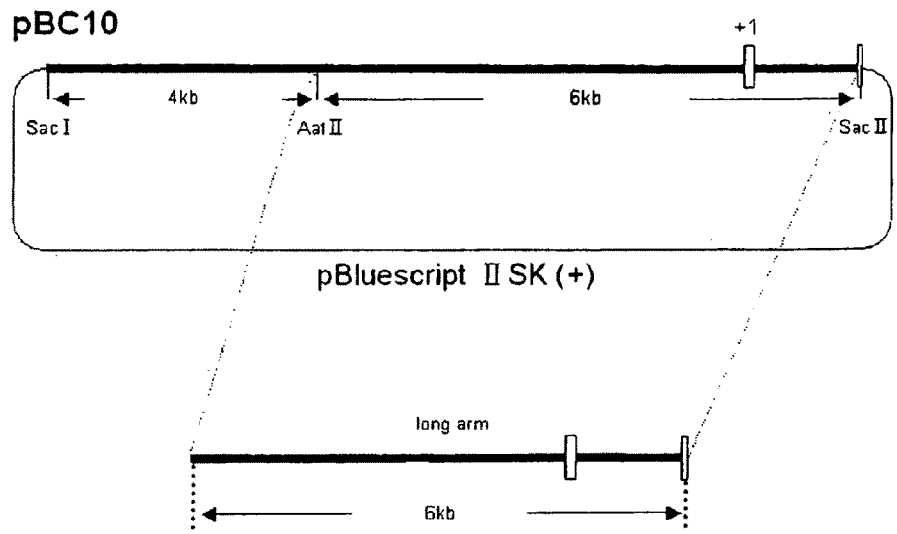
FIG. 11 shows the isolated 6 kb DNA fragment from the pBC10 vector digested with Aat II and Sac II restriction enzymes. The isolated 6 kb DNA fragment is used for a long arm of the pBCKI II vector cassette.
Figure 14:
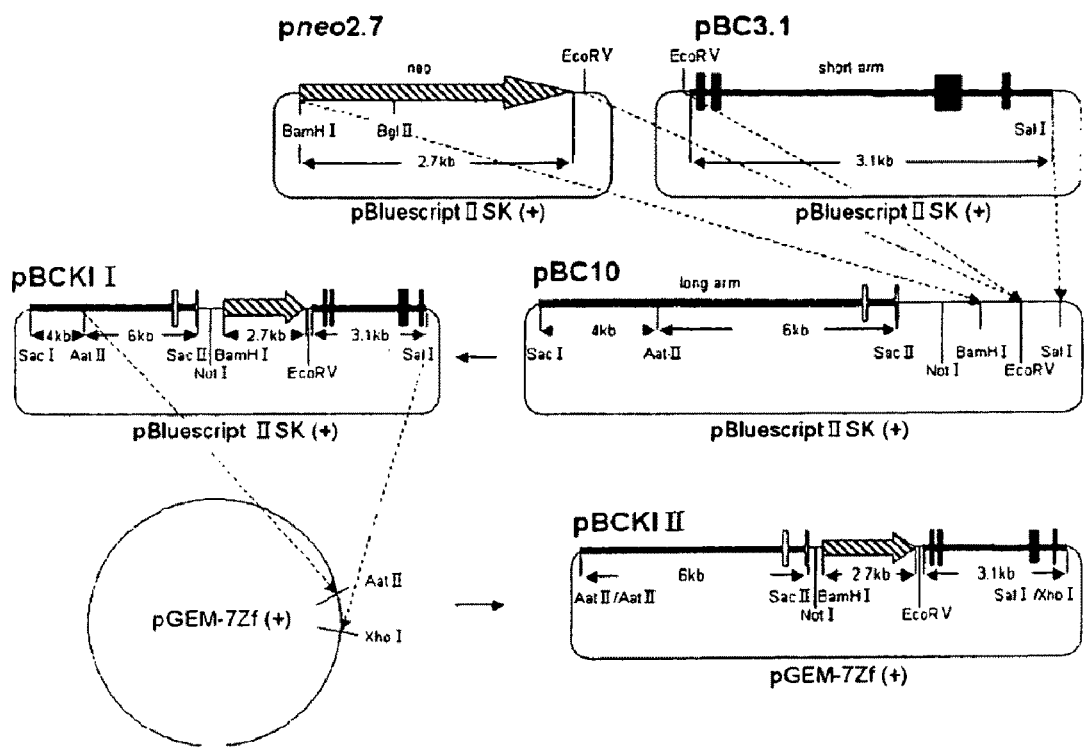
FIG. 14 shows the construction procedures of the pBCKI I and pBCKI II vector cassettes. The DNA fragments corresponding to a positive selection marker and short arm in pBluescript II SK(+) were digested with respective restriction enzymes, and then ligated into the BamH I EcoR V, and Sal I site of pBluescript II SK(+) vector harboring pBC10 DNA fragment. The resultant pBCKI I vector includes the 10 kb long arm, the selection marker gene and the short arm. To shorten long arm length of the pBCKI I, the DNA fragment digested with Aat II and Sal I restriction enzymes was ligated into Aat II and Xho I sites of pGEM7Zf(+) vector. The resultant pBCKI II vector includes the 6 kb long arm, the neo gene, and the short arm.

The pBC 10 vector construct (FIG. 9) as previously described (Sohn et al., J. Biotechnol., 103(1); 11-19, 2003) contains a 8 kb promoter of 5'-flanking sequence, the entire exon 1 and 2 kb intron 1 and 5'-UTR of exon 2 of the bovine beta casein in a pBluescript II SK(+) plasmid (Stratagene). The beta-casein gene region of the pBC 10 vector was used as a long arm (a first DNA region) of two invented vector cassettes, pBCKI I and pBCKI II. As shown in FIG. 10, a 10 kb beta-casein gene could be digested with Sac I and Sac II restriction enzymes and it was used as a long arm (a first DNA sequence) of the pBCKI I vector cassette (FIGS. 10 and 14). A 6 kb beta-casein promoter region digested with Aat II and Sac II restriction enzymes, including 4 kb promoter, untranslated exon 1, 2 and intron 1 of the bovine beta-casein gene, was used as a long arm (a first DNA sequence) of BCKI II (FIGS. 11 and 14).

Figure 12:
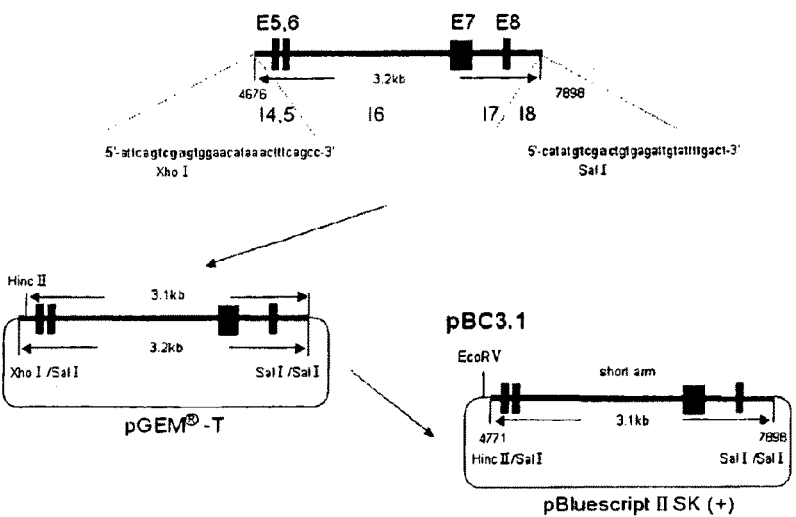
FIG. 12 shows construction procedures of the pBC3.1 vector applied for the short arm of pBCKI I and pBCKI II vector cassettes. The 3.2 kb DNA fragment including exon 5, 6, 7 and 8 of bovine beta-casein gene was prepared by PCR amplification using the primer set which has Xho I and Sal I sites (bold characters) from the bovine chromosomal DNA. The amplified PCR fragment was digested with Xho I and Sal I restriction enzymes and then ligated into the Sal I restriction enzyme site of pGEM-T vector (Promega). The 3.2 kb DNA fragment in the PGEM-T vector was digested with Hinc II and Sal I restriction enzymes and then ligated into Sal I site of pBluescript II SK(+) vector.
Figure 13:
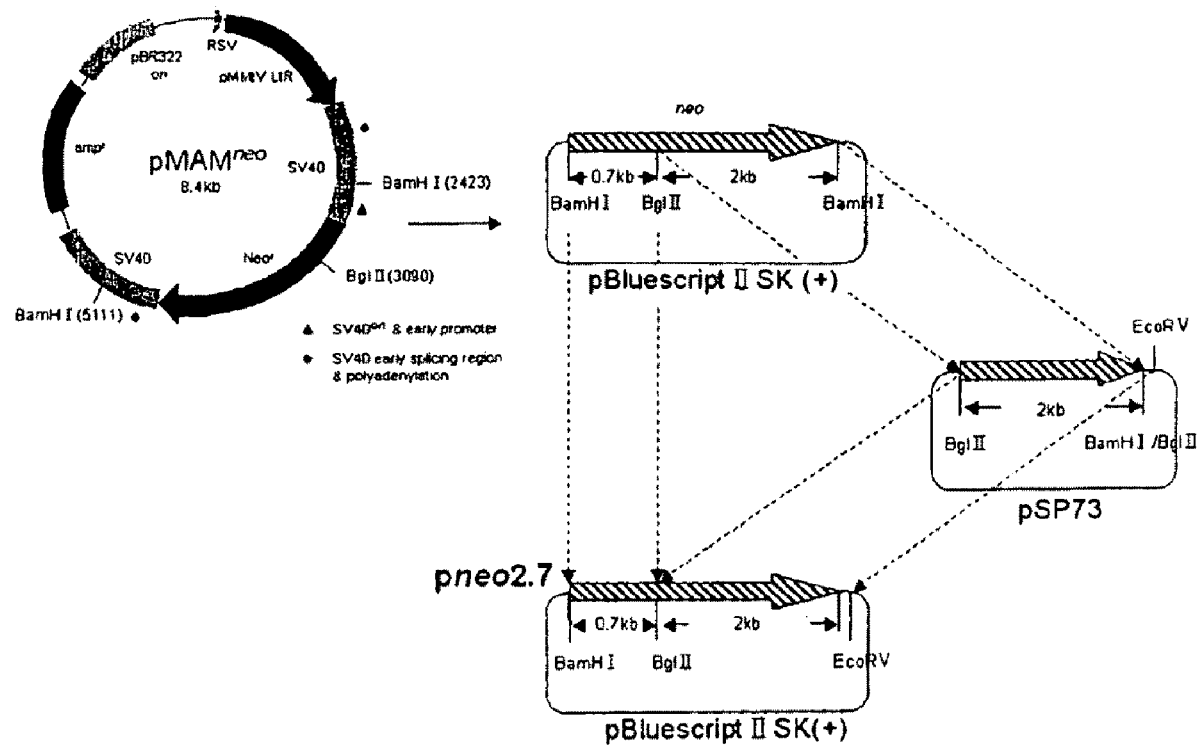
FIG. 13 shows the procedure obtaining the neo gene including the SV40 ori, the early promoter, the neomycin resistance gene, the SV40 early splicing region and polyadenylation site from a pMAMneo vector (CLONTECH). The 2.7 kb neo gene fragment digested with BamH I restriction enzyme was ligated into BamH I site of pBluescript II SK(+) vector. The 2 kb DNA fragment of the neo gene in a pBluescript II SK(+) vector was digested with Bgl II and BamH I restrction enzymes and ligated into Bgl II site of pSP73 vector (Promega). The 2 kb fragment of a pSP73 vector digested with Bgl II and EcoR V restriction enzymes was then re-ligated into Bgl II and EcoR V sites of the pBluescript II SK(+) vector containing the 0.7 kb neo gene to generate the pneo2.7 vector construct.

The pBC3.1 vector (FIG. 12) was constructed to utilize as a short arm of the vector cassettes of the invention. The 3.2 kb DNA fragments of the bovine beta-casein gene sequence (4676 to 7898), containing exons 5, 6, 7, 8 and introns 5, 6, 7 and partial introns 4 and 8, was amplified by PCR using bovine genomic DNA as the template. Sequences of the primers used for the PCR reaction are as follows:

```
Forward primer:
SEQ ID No 1:
5'-attcagtcgagtggaacataaactttcagcc-3'

Reverse primer:
SEQ ID No 2:
5'-catatgtcgactgtgagattgtattttgact-3'
```

Bold characters of the primer sequences depict that some bases were changed to generate Xho I and Sal I restriction enzyme sites.

The PCR product (FIG. 12) was digested with Xho I and Sal I restriction enzymes and ligated into the Sal I site of pGEM-T (Promega). To generate enzyme sites to insert into pBC10 vector, the 3.2 kb bovine beta-casein gene fragment in pGEM-T was digested with Hinc II and Sal I restriction enzymes. The resultant 3.1 kb fragment was ligated into Sal I site of pBluescript II SK(+) to generate the BC3.1 vector.

The neo gene fragment utilized as a selection marker also was inserted into pBC10 vector. To obtain the neo gene fragments including the SV40 ori, early promoter, the SV40 early splicing region and polyadenylation regions, a pMAMneo vector (CLONTECH) was digested with Bam H I restriction enzyme (FIG. 10). First, the resultant 2.7 kb DNA fragment was ligated into Bam H I site of the pBluescript II SK(+). Second, the 2 kb neo gene fragment in the ligated vector was digested with Bgl II and Bam H I restriction enzymes and then ligated into Bgl II site of the pSP73 (Promega). Finally, the 2 kb neo gene fragment in the pSP73 was digested with Bgl II and EcoR V restriction enzymes and then re-ligated into the Bgl II and EcoR V sites of the pBluescript II SK(+) harboring the 0.7 kb pMAMneo gene fragment. These DNA digestion and ligation steps were required for inserting the 2.7 kb neo gene fragment into the pBC10 vector (FIG. 14).

As shown in FIG. 11, pBCKI I and pBCKI II vector cassettes were accomplished by assembling pneo2.7 and pBC3.1 gene fragments into the pBC10 vector. The neo gene in pBluescript II SK(+) was digested with Bam H I and EcoR V restriction enzymes and then ligated into Bam H I and EcoR V sites of the pBC10 vector. The pBC3.1 vector was digested with EcoR V and Sal I restriction enzymes and then ligated into EcoR V and Sal I sites of the pBC10 vector including the ligated pMAMneo gene fragment to generate the PBCKI I vector cassette. The pBCKI I vector cassette was digested with Aat II and Sal I restriction enzymes and ligated into Aat II and Xho I sites of the pGEM-7Zf (Promega) to generate the pBCKI II vector cassette. Therefore, the pBCKI I and pBCKI II vector cassettes were constructed.

1-2 pBCKIDT I and pBCKIDT II Vector Construction

Figure 3:
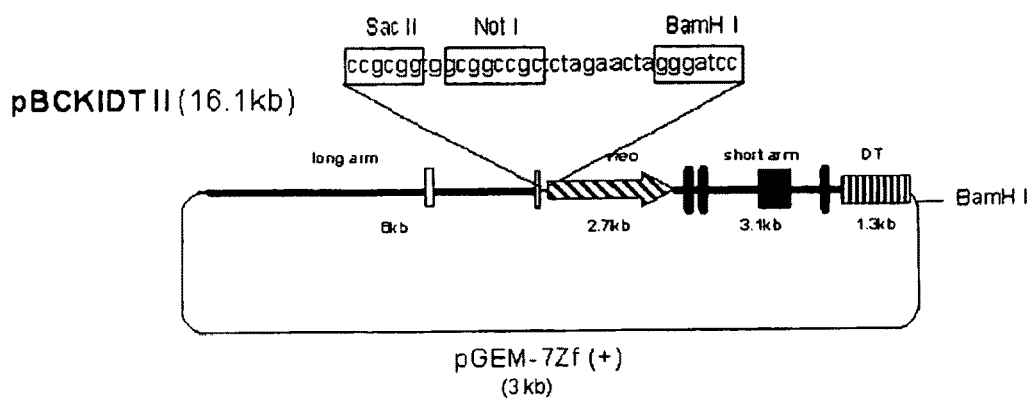
FIG. 3 depicts 160.1 kb pBCKIDT II vector cassette targeting the bovine beta-casein gene, derived from pGEM-7Zf (+) plasmid. The vector also includes Sac II, NotI, and BamH I restriction sites in front of neo gene and BamH I site at the back of short arm region. In addition, 1.3 kb diphtheria toxin (DT) gene as a negative selection marker is inserted.
Figure 4:
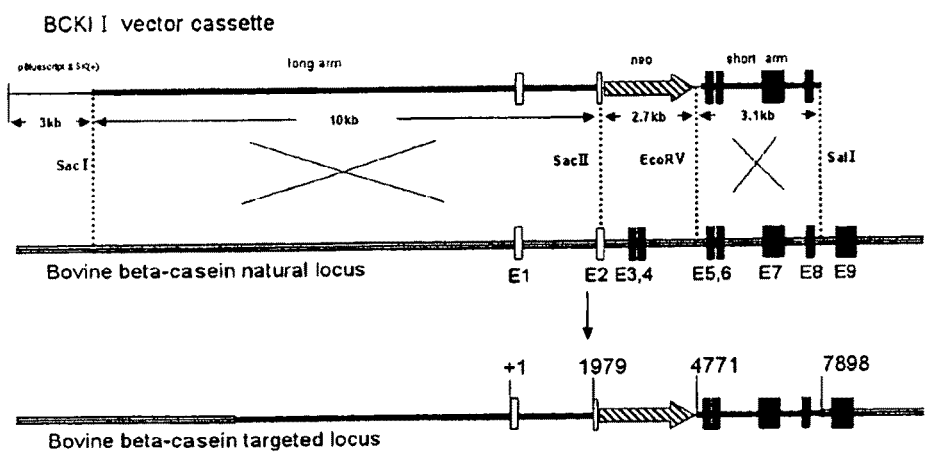
FIG. 4 shows homologous recombination between pBCKI I vector and beta-casein gene in genome. Double crossover results in the replacement of the endogenous beta-casein gene with the sequences in the vector cassette.
Figure 15:
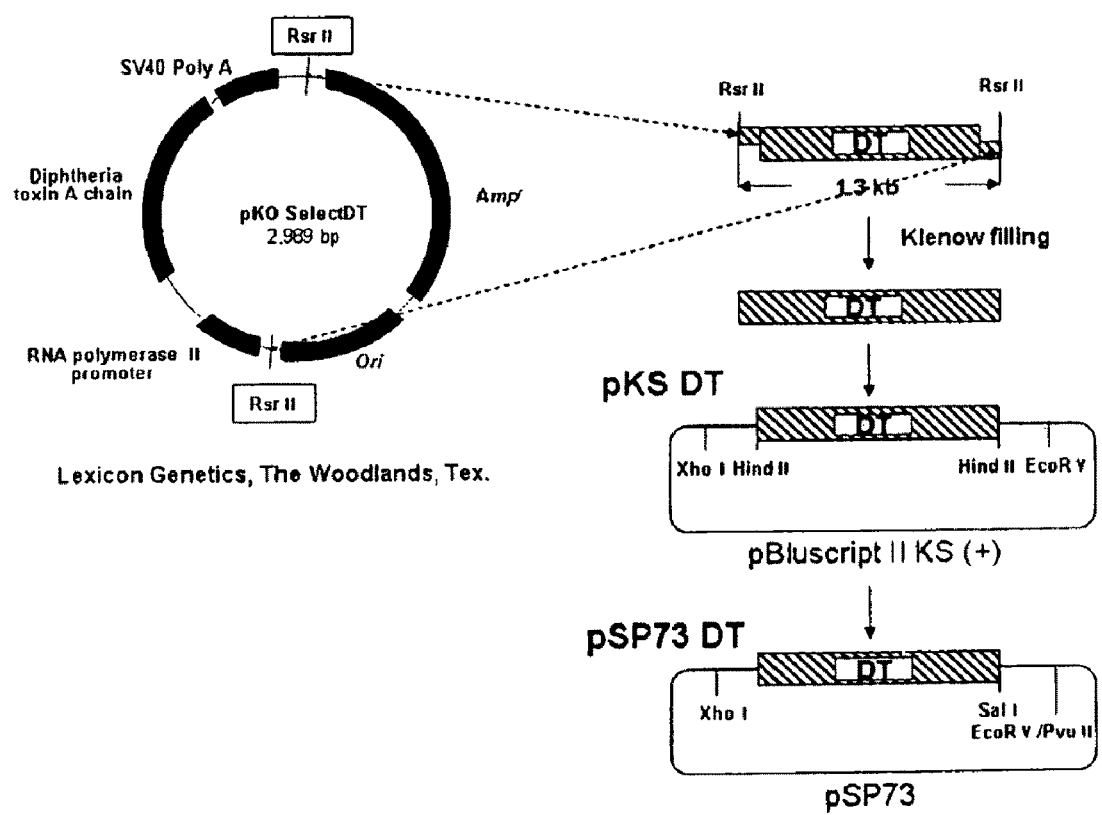
FIG. 15 shows the procedure obtaining the DT gene, inserted into pBCKIDT II vector, from pKO SelectDT (Lexicon Genetics). Using restriction enzyme, Rsr II, diphtheria toxin A (DT) gene containing SV40 Poly A and RNA polymerase II promoter was isolated. After klenow-filling the isolated DT gene, it was inserted into Hind II sites of pBluescript II SK(+) vector (Stratagene), generating pSK DT vector. The DT gene in the pSKDT vector was digested with Xho I and EcoR V restriction enzymes and ligated into Xho I and Pvu II sites of a pSP73 vector (Promega) to generate the pSP73DT vector construct.
Figure 16:
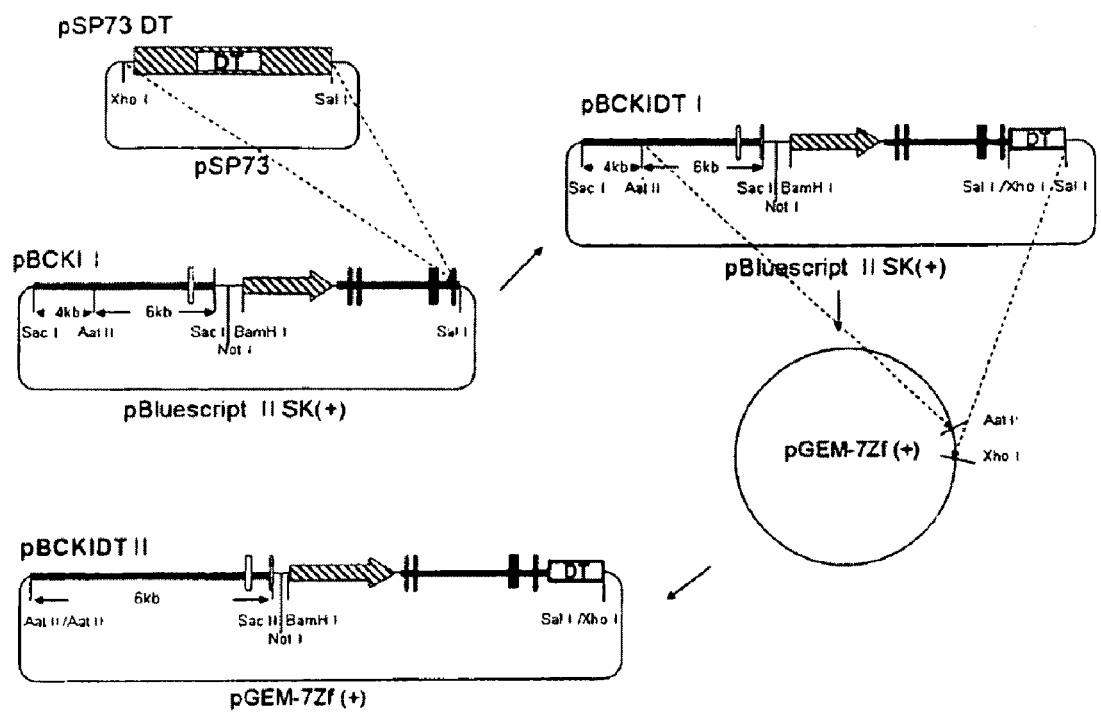
FIG. 16 shows the construction procedures of the pBCK-IDT II vector cassette. DT gene in pSP73DT vector was digested with restriction enzyme, Xho I and Sal I and then ligated into Sal I site of pBCKI I vector cassette, generating pBCKIDT I vector. The resultant pBCKIDT I vector was digested with Aat II and Sal I and then ligated into Aat II and Xho I sites of pGEM-7Zf(+) vector (Promega), generating pBCKIDT II vector cassettes.

A negative selection marker, DT gene, was inserted into the above vectors (FIGS. 3 and 16). As using pBCKIDT I and pBCKIDT II vectors harboring a negative selection marker, non-targeted cell clones are reduced because most cell clones which have integrated the vectors at a random location are killed by toxicity of DT gene (FIGS. 3 and 16). The DT gene utilized in the invention was isolated from pKO SelectDT vector (Lexicon Genetics, The Woodlands, Tex.). Using a restriction enzyme, Rsr II, the Diphtheria toxin A chain (DT) gene with SV 40 Poly A and RNA polymerase II promoter was isolated. After klenow-filling the isolated DT, gene, it was inserted into Hind II restriction sites of pBluescript II KS (+) (Stratagene), resulting pKS DT vector. DT gene in the pKS DT vector was digested with Xho I and EcoR V and ligated into Xho I and Pvu II sites of pSP73 vectors (Promega), resulting pSP73 DT vector (FIG. 15). The DT gene in pSP73 DT vector was digested with Xho I and Sal I and then, inserted into Sal I site of pBCKI I vector cassette, resulting pBCKIDT I vector. The pBCKIDT I vector was digested with Aat II and Sal I and ligated into Aat II and XhoI sites of pGEM-7Zf (+) (Promega), resulting pBCKIDT II vector cassette (FIG. 16).

The fidelity of the targeting-vector cassettes was confirmed again by DNA sequencing and enzyme mapping on all regions of synthetic DNAs and all junctions of the ligated DNA fragments.

EXAMPLE 2

Construction of pBCTPOKI I and pBCTPOKI II

As shown in FIGS. 17, 18 and 19, the 1 kb Human TPO cDNA plus 300 bp bovine growth hormone was inserted pBCKI I, pBCKI II, and pBCKIDT II vector cassettes. The 1.3 kb foreign gene harboring Sac II and Not I sites was ligated into the Sac II and Not I sites of the pBCKI, pBCKI II, and pBCKIDT II vectors, respectively, thereby generating the targeting vectors, named as pBCTPOKI I, pBCTPOKI II, and pBCTPOKIDT II (FIGS. 17, 18, and 19). Particularly, *Escherichia coli* cells transformed with the pBCTPOKIDT II vectors were deposited with the Korean Collection for Type Cultures (KCTC) located in #52, Oun-dong, Yusong-ku, Taejon 305-333, Republic of Korea on Oct. 17, 2005, under the accession number KCTC 10864BP.

EXAMPLE 3

Transfection of pBCTPOKI I, pBCTPOKI II, and pBCTPOKIDT II Vector Constructs into Bovine Embryonic Fibroblasts (bEF) and Bovine Ear Skin Fibroblasts (bESF)

3-1 Introduction of Linearized Vectors

Figure 20:
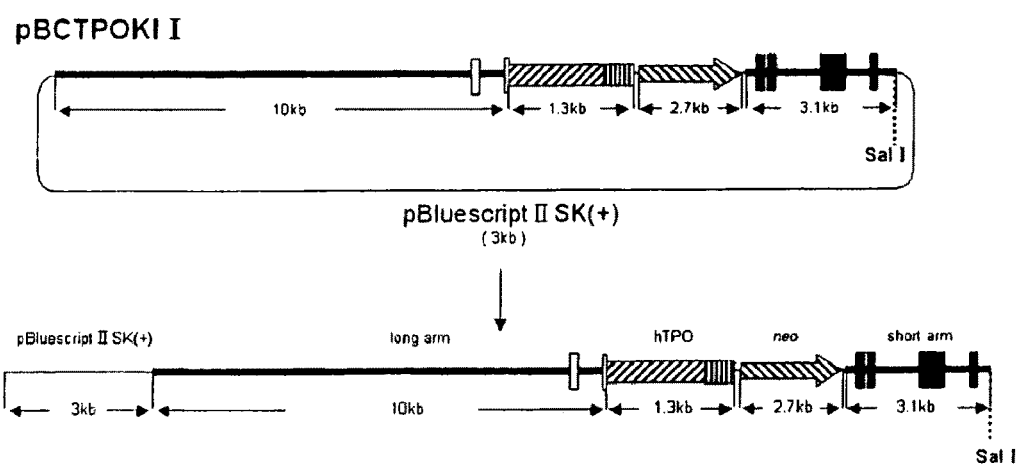
FIG. 20 shows the linearized pBCTPOKI I vector to be used for transfection after Sal I digestion.
Figure 21:
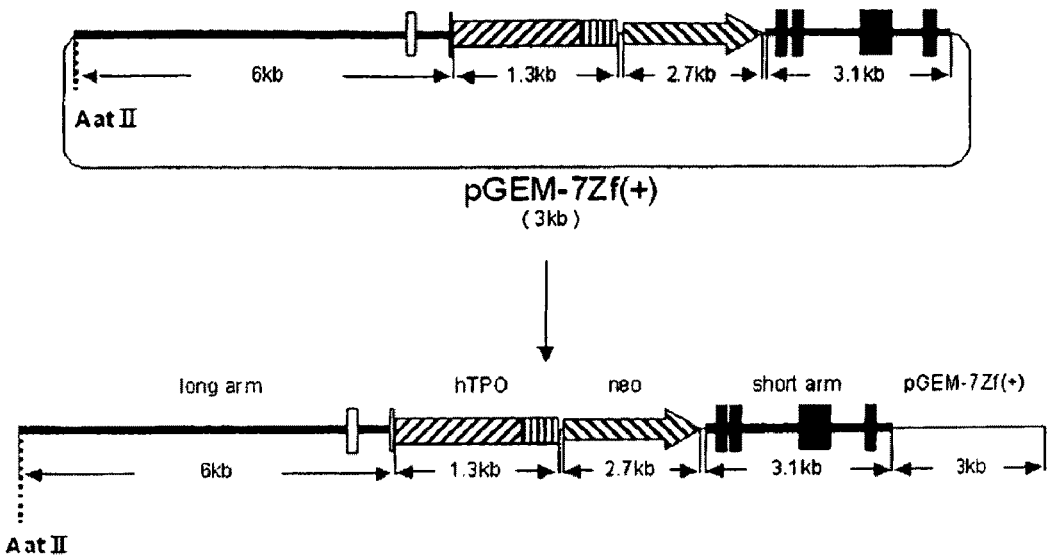
FIG. 21 shows the linearized pBCTPOKI II vector to be used for transfection after Aat II digestion.

The plasmid DNAs, pBCTPOKI I and, pBCTPOKI II, were purified by using "QIAfilter Plasmid Midi kits" (Qiagen) and then closed circular DNAs were isolated by an equilibrium centrifugation in CsCl-ethidium bromide gradient. The isolated pBCTPOKI I and pBCTPOKI II plasmids were linearized by digestion of Sal I (FIG. 20) and Aat II (FIG. 21) restriction enzymes, respectively, and then purified by ethanol precipitation. Finally, the concentrations of the purified DNAs were determined by using a spectrophotometer.

The linearized pBCTPOKI I and pBCTPOKI II constructs were introduced into the bEF and bESF at passage 2 or 3 by using Lipofectamine 2000 reagent (Invitrogen). For bEF, we tested three different transfection reagent volumes such as 2, 4 and 10 µl, and two different DNA concentrations such as 2 and 4 µg. For bESF, 2, 4 and 10 µl transfection reagent volumes and 1, 2 and 4 µg DNA concentrations were tested. The somatic cells were exposed to the transfection reagent-DNA complexes for 24 h.

The somatic cells were cultured in Dulbecco Modified Eagle Medium (Gibco, Invitrogen corporation) supplemented with 10% FBS (Hyclone), 0.001% Gentamicine (Gibco, Invitrogen corporation) and 1% MEM Non-Essential Amino Acid (Gibco, Invitrogen corporation) and the culture medium was exchanged everyday. The cells were incubated at 37° C., 5% $CO_2$ in air. The volume of cell culture medium was different depending on the plate types used as shown below.

| 96 well | 48 well | 24 well | 12 well | 6 well | 100 mm dish |
|---------|---------|---------|---------|--------|-------------|
| 0.2 ml  | 0.5 ml  | 1.0 ml  | 1.5 ml  | 3 ml   | 10 ml       |

The cells grown to confluence were treated with 1× Trypsin-EDTA (Gibco, Invitrogen corporation) solution at 37° C. for 3 min and then washed twice with Dulbecco's Phosphate-Buffered Saline (Gibco, Invitrogen corporation) Cell colonies detached by 1× Trypsin-EDTA treatment were dissociated by gentle pipetting and then transferred into the more wider plates for proliferation. The volumes of 1× Trypsin-EDTA solution used depends on cell culture plate types as shown below

| 96 well | 48 well | 24 well | 12 well | 6 well | 100 mm dish |
|---------|---------|---------|---------|--------|-------------|
| 50 µl   | 100 µl  | 150 µl  | 200 µl  | 500 µl | 1 ml        |

The procedure of the experiment is shown below:

| | |
|---|---|
| Day 1 | $5.5 \times 10^5$ bEF cells and $3.6 \times 10^5$ bESF cells at passage 2 or 3 onto 6-well culture plates were transfected with the linearised BCTPOKI I and BCTPOKI II DNAs using Lipofectamine 2000 reagent (Invitrogen) in 2 ml of OPTIMEM I Reduced Serum Medium (Gibco, Invitrogen corporation) according to the procedure recommended by the manufacturers. |
| Day 2 | Transfected cells were split into two 100 mm culture dish and further cultured. |
| Day 3 | 0.8-1.5 mg/ml G418 (Gibco, Invitrogen coporation) was added to the culture medium. |
| Day 4-14 | Colonies of, approximately, 2-3 mm in diameter were picked and individually replated into wells of 96 well culture plates. |

The cells grown until confluent in 96-well plates were transferred to 48 well culture plates and then were gradually expanded in 24 well, 12 well, 6 well and 100 mm culture plates.

In 6 well plates, approximately half of the transfected cells were picked for PCR reactions and the other was transferred into two wells of a 6 well culture plate.

3-2 Introduction of Linearized Vectors after Deleting Plasmid Vectors

Figure 22:
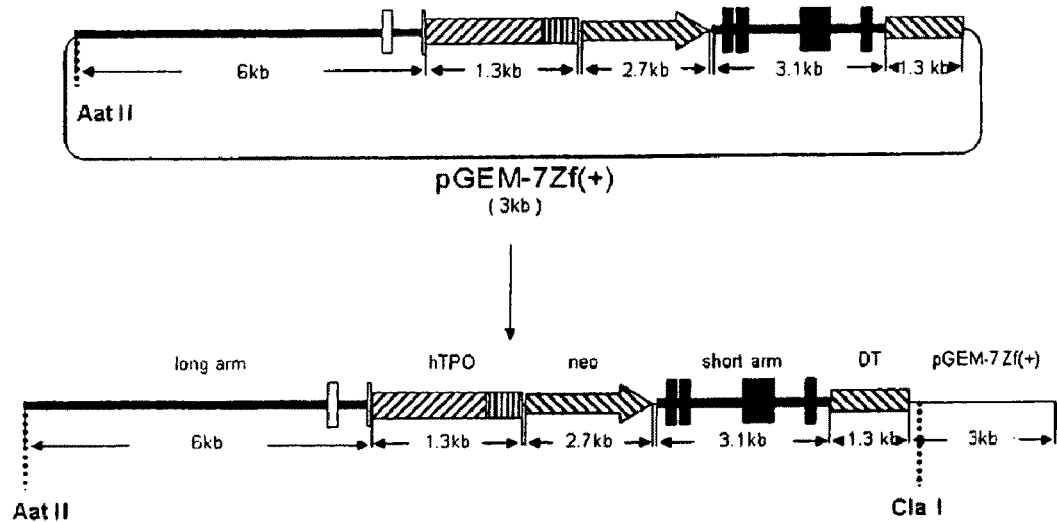
FIG. 22 shows the linearized pBCTPOKIDT II vector to be used for transfection after deleting a plasmid vector by Aat II and Cla I digestion.
Figure 23:
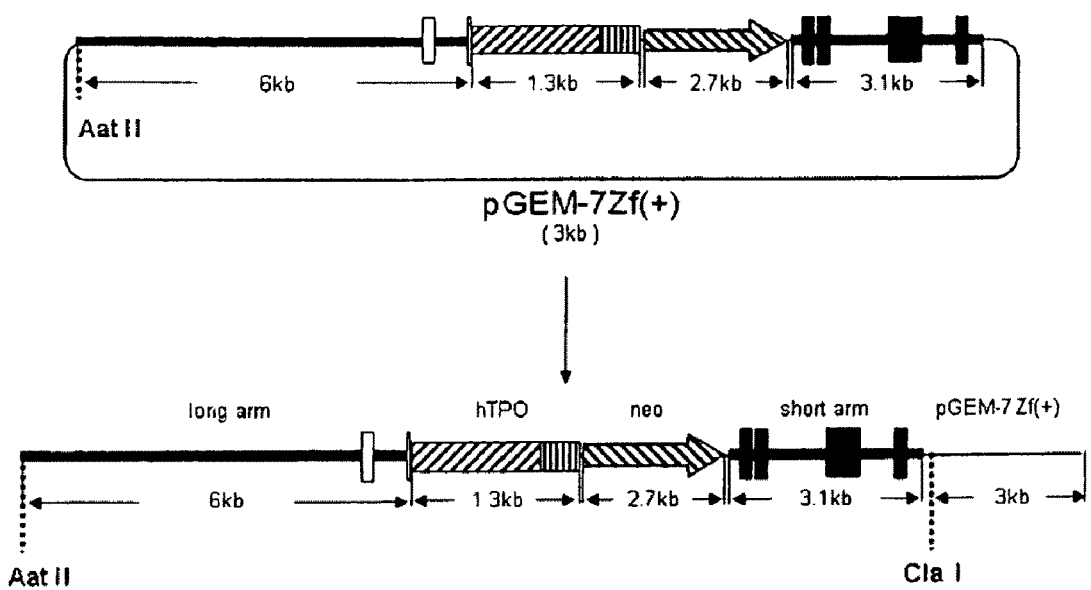
FIG. 23 shows the linearized pBCTPOKI II vector to be used for transfection after deleting a plasmid vector by Aat II and Cla I digestion. Whereas the pBCTPOKI II vector, described in FIG. 21, was simply linearized and transfected into cells with a plasmid vector, the pBCTPOKI II vector, described here, was transfected into cells after deleting a plasmid vector by two restriction enzyme digestion.
Figure 24:
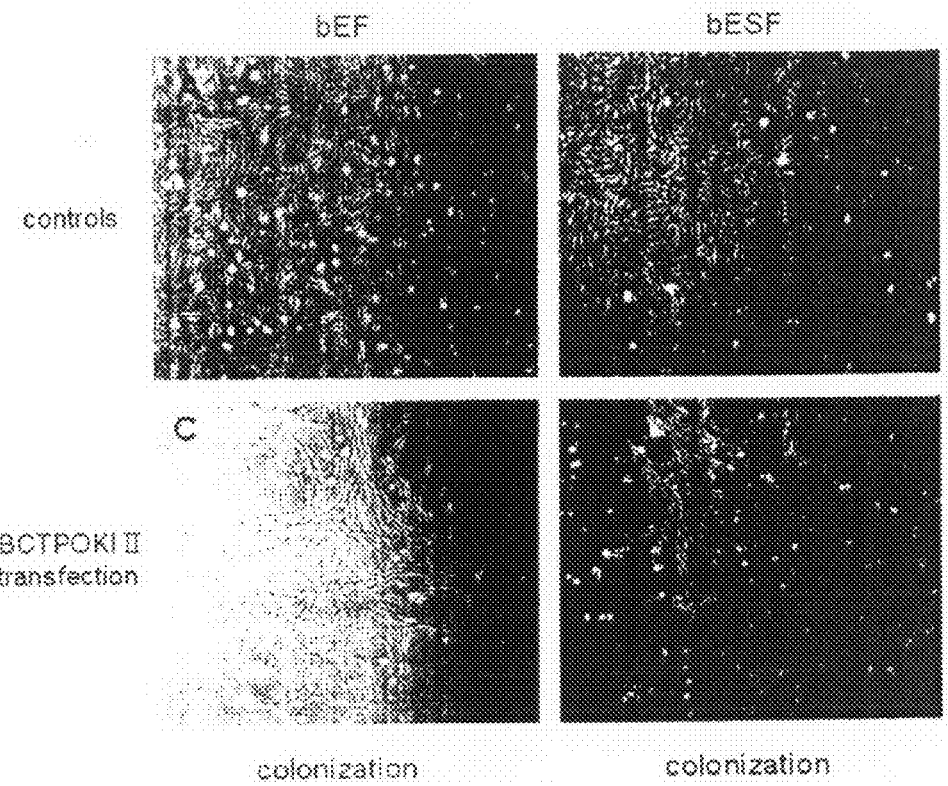
FIG. 24 is photographs showing morphologies of bovine embryonic fibroblasts (bEF) and bovine ear skin fibroblasts (bESF). A and B are non-transfected (normal) cells, bEF and bESF, respectively, cultured to confluence. C and D show the colony formed after transfection of the targeting vector into bEF and bESF, respectively. After the targeting vector which has antibiotic resistance gene, neo gene, is introduced into bEF and bESF using the Lipofectamine™ 2000 reagent (Invitrogen) method, the transfected cells were treated with G418 (Gibco, Invitrogen corporation) and then only the survived colonies were subject to analyses of the inserted foreign genes.
Figure 25:
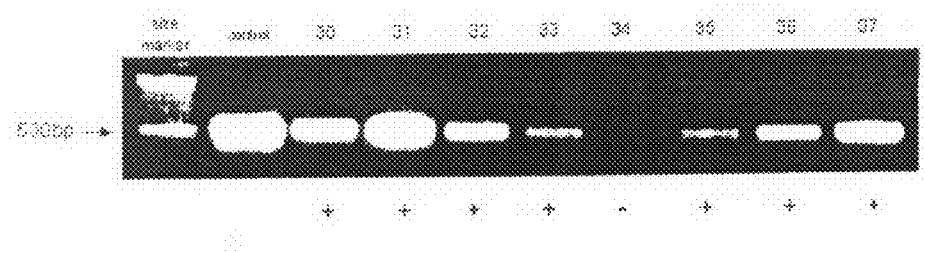
FIG. 25 shows PCR analysis of the survived colonies after pBCKI II transfection. The positive signals for the 500 bp PCR fragment indicated by an arrow represent transfected cell clones, were denoted as "+" and the negative signals were denoted as "−". The pBCTPOKI II vector of the present invention was used as a positive control and the PCR was amplified with the primers specific for hTPO gene.
Figure 26:
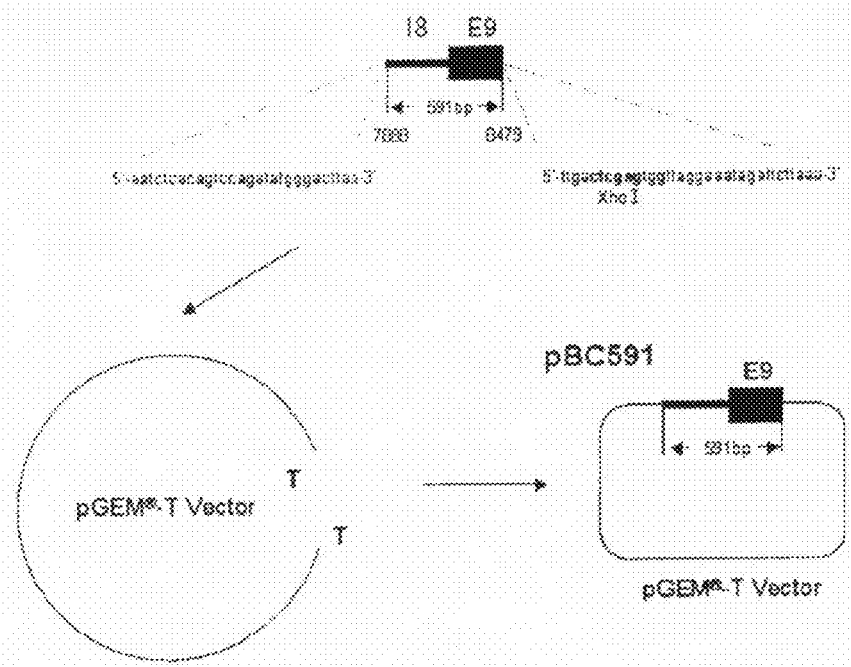
FIG. 26 and FIG. 27 depict construction procedures of the pneoBC3.7 vector to be used as the control for long-range PCR analysis. The 591 bp DNA fragment harboring intron 8 and exon 9 corresponding to bases 7888 to 8479 of bovine beta-casein gene was prepared separately by PCR amplification using a primer set from the bovine chromosomal DNA. The 3' primer has Xho I site depicted as bold characters. The amplified PCR fragment was ligated into pGEM-T vector to generate the pBC591 vector construct. The pBC591 vector was digested with Sal I and Xho I restriction enzymes, and then the resultant DNA fragment was ligated into Sal I site of the pBC3.1 vector. At the same time, the pneo2.7 vector digested with BamH I and EcoR V restriction enzymes, and then the resultant DNA fragment was ligated into the pBC3.1 vector digested with BamH I and EcoR V restriction enzymes to generate the pneoBC3.7 vector. The arrows show primer set for 4 kb long-range PCR analysis.

The plasmid vector regions of pBCTPOKI II and pBCTPOKIDT II vector constructs were deleted by digesting with restriction enzymes, Aat II and Cla I, and then, transfected into bESF and bEF cells as referred above (FIGS. 22 and 23).

EXAMPLE 4

Identification of the Transfected Cell Clones by PCR Analysis

To screen transgenic cell lines, G418 resistant-colony cells were analyzed by PCR. Genomic DNAs were purified from half of the cells in 6 well plates using "AccuPrep Genomic DNA Extraction Kit" (Bioneer) and PCR was carried out using "AccuPower PCR Premix" (Bioneer). Primer sets for human TPO cDNA and thermal cycling conditions are shown below:

```
                                        SEQ ID No 3
Forward primer   GGA GCT GAC TGA ATT GCT CCT CGT SEQ ID No 4
Reverse primer   CCT GAC GCA GAG GGT GGA CCC TCC
```

| | | |
|---|---|---|
| 1 cylcle of | 94° C. | 2 min |
| 30 cycles of | 94° C. | 1 min |
| | 65° C. | 30 sec |
| | 72° C. | 45 sec |
| 1 cycle of | 72° C. | 10 min |

As results of the PCR, most cell clones resistant to G418 identified as transgenic dell (FIG. 17).

EXAMPLE 5

Long-range PCR to Detect Targeted Cell Clones

Long-range PCR was employed to determine the gene-targeted cell clones among transgenic cell clones. Genomic DNAs from each transgenic cell clone were purified using "AccuPrep Genomic DNA Extraction Kit" (Bioneer) or exposed by 3-4 cycles of freezing in liquid nitrogen and thawing in boiling water. Long-range PCR was performed using "AccuPower HL PCR Premix" (Bioneer).

Figure 5:
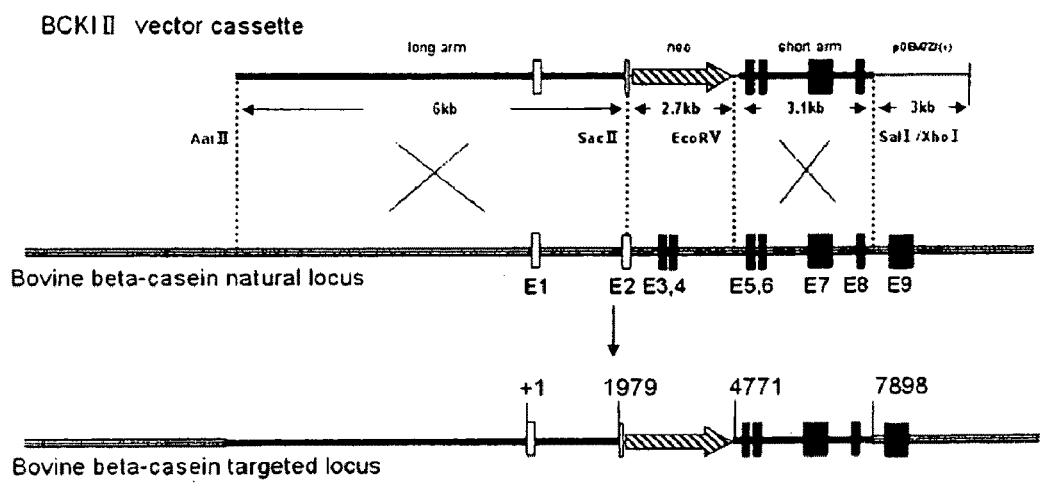
FIG. 5 shows homologous recombination between pBCKI II vector and a beta-casein gene in genome. A partial sequence of a beta casein gene locus in genome is replaced with a partial sequence in a vector cassette as result of a double crossover event.
Figure 6:
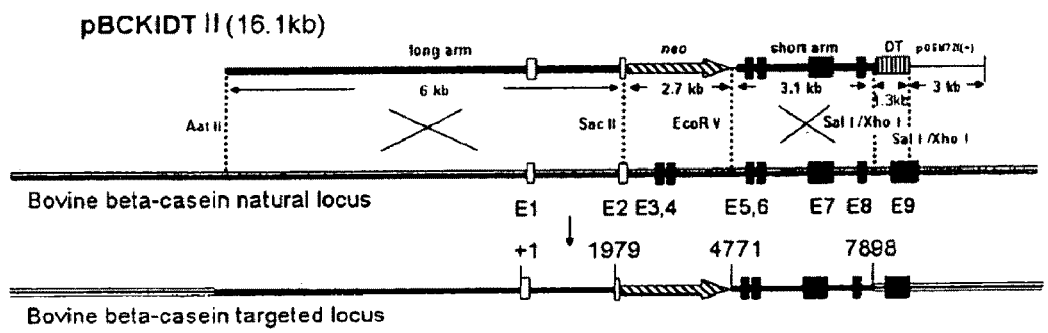
FIG. 6 shows homologous recombination between pBCK-IDT II vector and a beta-casein gene in genome. Double crossover results in the replacement of the endogenous beta-casein gene with the sequences in the vector cassette. As results of homologous recombination events, DT gene is deleted.
Figure 7:
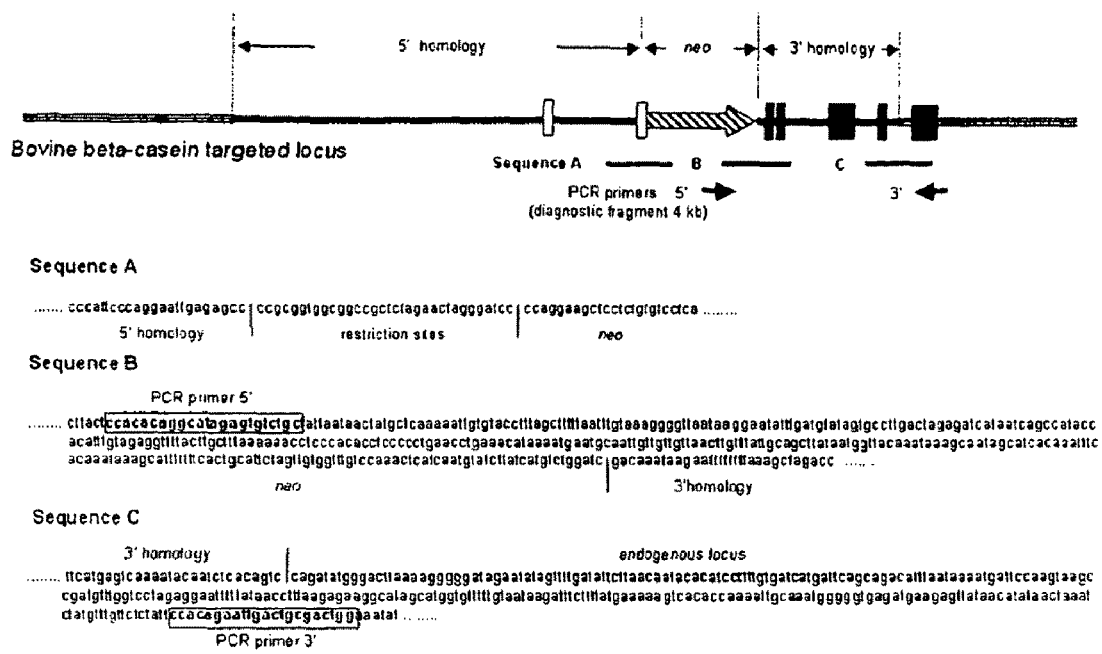
FIG. 7 shows PCR screening strategy used to identify gene targeting events at the bovine beta-casein locus and the DNA sequences spanning the junctions of the targeted beta-casein locus and the restriction sites in the targeting vector cassettes, pBCKI I and pBCKI II. The upper portion shows the approximate position of two primers used to amplify the 4 kb fragment, from the neo gene region unique to the beta-casein gene targeting vectors to the endogenous beta-casein locus which is not used in the vector cassettes. Sequence A shows a portion of DNA sequence spanning the junction between the long arm region and the neo gene. Sequence B shows a portion of DNA sequence spanning the junction between the neo gene and the short arm region. The position and orientation of the 5' PCR primer is shown. Sequence C shows a portion of DNA sequence spanning the junction between the short arm region and the endogenous beta-casein gene locus which is excluded from the BCKI I and BCKI II vectors. The position and orientation of the 3' PCR primer is shown.
Figure 8:
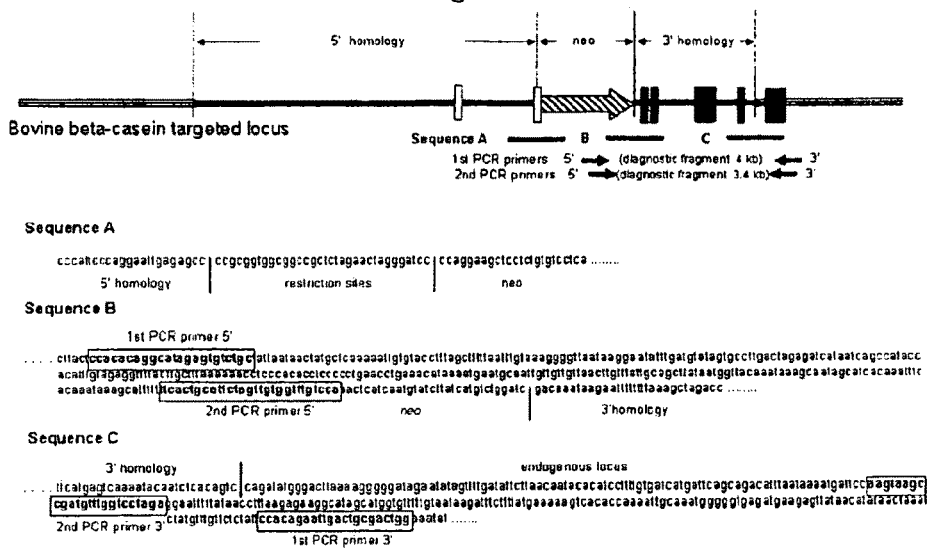
FIG. 8 shows PCR screening strategy used to identify gene targeting events at the bovine beta-casein locus and the DNA sequences spanning the junctions of the targeted beta-casein locus and the restriction sites in the targeting vector cassette, pBCKIDT II. The upper portion shows the approximate position of two primer sets used to amplify the 4 and 3.4 kb fragments, from the neo gene region unique to the beta-casein gene targeting vectors to the region endogenous beta-casein locus which is not used in the vector cassettes. Here, after amplifying 4 kb PCR fragments using the first primer set, 3.4 kb PCR fragments were amplified using the second primer set for a small volume of DNA samples. Sequence A shows a portion of DNA sequence spanning the junction between the long arm region and the neo gene. Sequence B shows a portion of DNA sequence spanning the junction between the neo gene and the short arm region. The positions and orientations of the 5' PCR primers are shown. Sequence C shows a portion of DNA sequence spanning the junction between the short arm region and the endogenous beta-casein gene locus which is excluded from the BCKI I and BCKI II vectors. The positions and orientations of the 3' PCR primers are shown.

As shown in FIG. 5, the 5' primer was designed to bind at the 3' end of neo gene within the transfected vector constructs and the 3' primer to bind at the intron 8 of bovine beta casein gene which exists in the endogenous region, not in the vector construct. The gene targeted cell clones showed represented 4 kb PCR products on 1% agarose gel. The sequences of a primer set and thermal cycling conditions are shown below:

```
                                     SEQ ID No 5
Forward primer:   5'-ccacacaggcatagagtgtctgc-3'

SEQ ID No 6
Reverse primer:   5'-ccacagaattgactgcgactgg- 3'
```

| | | |
|---|---|---|
| 1 cylcle of | 92° C. | 2 min |
| 35 cycles of | 92° C. | 20 sec |
| | 65° C. | 45 sec |
| | 68° C. | 3 min |
| 1 cycle of | 68° C. | 10 min |

Bovine-beta casein gene targeting efficiency was compared in examples 3-1 and 3-2.

Figure 28:
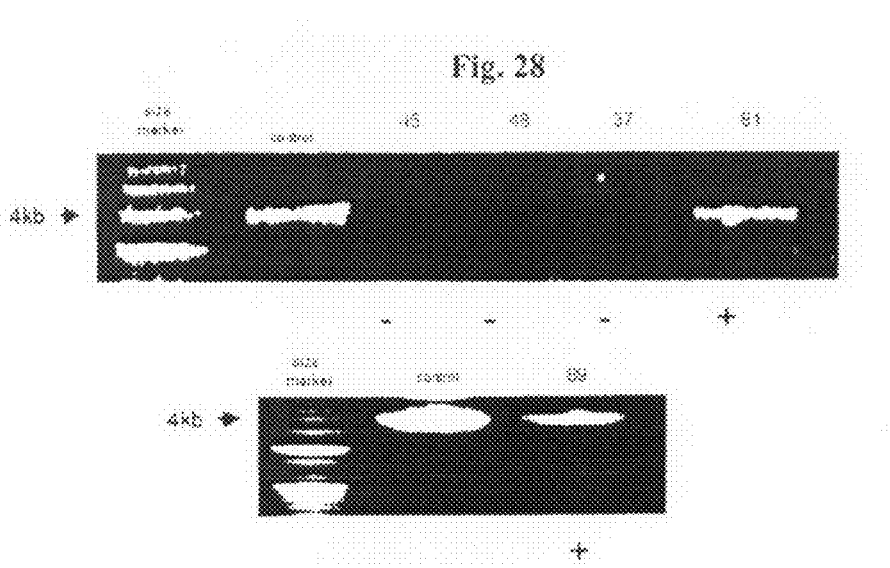
FIG. 28 shows the results of long-range PCR analyses of the bESF cell colonies transfected with pBCTPOKI II. The positive signals for the 4 kb indicated by arrows represent targeted cell clones, were detected in two colonies, "81" and "89", and the other colonies showed negative signals (−). The pneoBC3.7 vector was used as a positive control.

In example 3-1, two cell clones were identified to be gene-targeted (FIG. 28).

As shown in examples 3-1, 41 single colonies were isolated after the transfection of the pBCTPOKI I vector into the somatic cells. Among these cells, 38 colonies (93%) were identified to be transgenic, but no targeted colonies (0%) were detected. 31 single colonies were isolated after transfection of the pBCTPOKI II vector into the somatic cells. Among these, 29 colonies(94%) were identified as transgenic cells, and 2 colonies (7%) were identified to be gene targeted with BCT-POKI II vector at the endogenous bovine beta-casein gene locus in genome (Table 1 & FIG. 28).

TABLE 1

Transfection and targeting efficiencies of BCTPOKI I and BCTPOKI II vectors

| | Cell types | BCTPOKI I | | BCTPOKI II | |
|---|---|---|---|---|---|
| No. of analyzed colonies | bEF | 23 | 41 | 2 | 31 |
| | bESF | 18 | | 29 | |
| No. of transgenic colonies | bEF | 22 (96%) | 38 (93%) | 1 (50%) | 29 (94%) |
| | bESF | 16 (89%) | | 28 (97%) | |
| No. of targeted colonies | bEF | 0 (0%) | 0 (0%) | 0 | 2 (7%) |
| | bESF | 0 (0%) | | 2 | |

Figure 27:
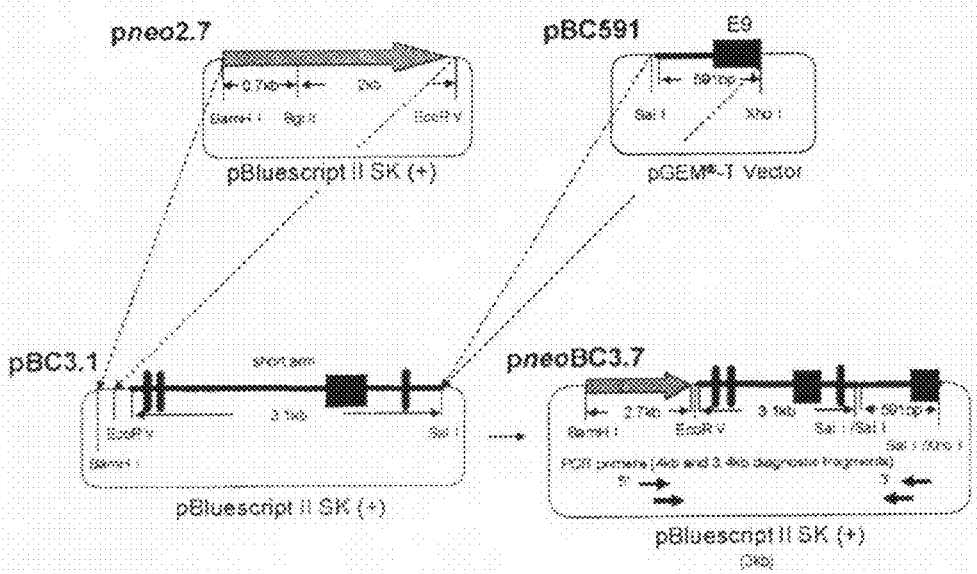
Figure 29:
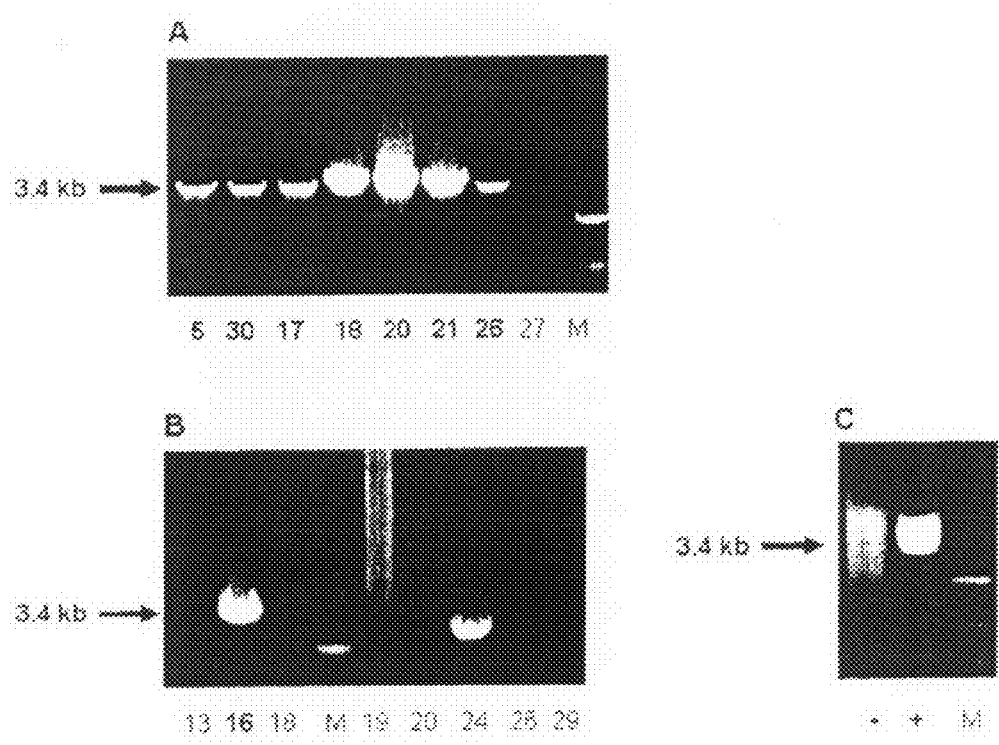
FIG. 29 shows the results of long-range PCR analyses of the bESF cell colonies transfected with pBCTPOKI II and pBCTPOKIDT II. The positive signals for the 3.4 kb indicated by arrows represent targeted cell clones. The first PCR analysis was performed from approximately five cells and then the second PCR analysis was performed from the first PCR products, showing resultant 3.4 kb positive signals (FIG. 8). A is the results of long-range PCR analyses of cell colonies transfected with pBCTPOKIDT II vector and the number 5, 30, 17, 18, 20, 21, and 26 cell colonies were identified to be gene-targeted. B is the results of long-range PCR analyses of cell colonies transfected with pBCTPOKI II and the number 16 cell colony was identified to be gene-targeted. C is the results of long-range PCR analyses of wild-type bovine genomic DNA used as a negative control (−) and pneoBC3.7 vector used as a positive control (+).

As shown in examples 3-2, pBCTPOKI II and pBCTPOK-IDT II vectors were transfected into bEF and bESF cells and targeted cell clones were confirmed using long-range PCR analysis. Here, for small volume of DNA samples, secondary PCR analysis was performed (FIGS. 27 and 29).

Thermal cycling conditions of secondary PCR reaction are same as those of example 5. The targeted cell clones showed represented 3.4 kb PCR products on 1% agarose gel. The sequences of a primer set of secondary PCR reaction are shown below:

```
Forward primer:
5'-ttcactgcattctagttgtggtttgtcca-3'   SEQ ID No 8

Reverse primer:
5'-tctaggaccaaacatcggcttactt-3'.      SEQ ID No 9
```

As shown in FIG. 29 A, the number 5, 30, 17, 18, 20, 21, and 26 bESF cell clones transfected with pBCTPOKIDT II vectors were identified to be targeted. B shows that the number 16 bESF cell clone transfected with pBCTPOKI II vector is targeted. C is the results of long-range PCR analyses of wild-type bovine genomic DNA used as a negative control (−) and pneoBC3.7 vector used as a positive control (+)

pBCTPOKI II and pBCTPOKIDT II vectors were transfected into bEF and bESF cells and targeting efficiencies were compared. 18.2% (10/55) bEF cell clones transfected with pBCTPOKI II vectors and 41.4% (12/29) bEF cell clones transfected with pBCTPOKIDT II vectors were identified to be gene-targeted, showing targeting efficiency by the pBCT-POKIDT II vectors is 2.3-fold (41.4%/18.2%) higher than that by the pBCTPOKI II vectors. And, 5.7% (12/212) bESF cell clones transfected with pBCTPOKI II vectors and 36.6% (63/172) bESF cell clones transfected with pBCTPOKIDT II vectors were identified to be gene-targeted, showing targeting efficiency by the pBCTPOKIDT II vectors is 6.4-fold (36.6%/5.7%) higher than that by the pBCTPOK II vectors. The average targeting efficiency of the pBCTPOKIDT II vectors in both cell types was 4.5-fold (37.3%/8.3%) higher than that of pBCTPOKI II vectors (Table 2), indicating the pBCKIDT II vector cassettes are highly efficient bovine beta-casein gene-targeting vectors. In addition, the targeting efficiency by pBCTPOKIDT II vectors in bEF cells was 3.3-fold higher (41.4%/12.7%) than the that by previous targeting vectors, in goat fetal fibroblasts (SHEN Wei et al., Chinese Journal of Biotechnology, 20(3); 361-365, 2004), indicating the invented vectors are highly efficient gene-targeting vectors.

TABLE 2

Transfection and targeting efficiencies of
pBCTPOKI II and pBCTPOKIDT II vectors

|  | Cell types | No. cell clones Analyzed | N0. cell clones targeted | % | % |
|---|---|---|---|---|---|
| pBCTPOKI II | bEF | 55 | 10 | 18.2% | 8.3% |
|  | bESF | 212 | 12 | 5.7% |  |
| pBCTPOKIDT II | bEF | 29 | 12 | 41.4% | 37.3% |
|  | bESF | 172 | 63 | 36.6% |  |

EXAMPLE 6

Southern Blot Analysis to Reconfirm Targeted Cell Clones

Using vectors described example 1, bovine beta-casein gene targeting was accomplished, following methods referred to example 3. As results, targeting efficiency was various, depending on types of vectors and transfected cells.

Here, both cell clones targeted with pBCTPOKI II vectors, using methods of example 3-1, were re-analyzed by the southern blotting.

Figure 30:
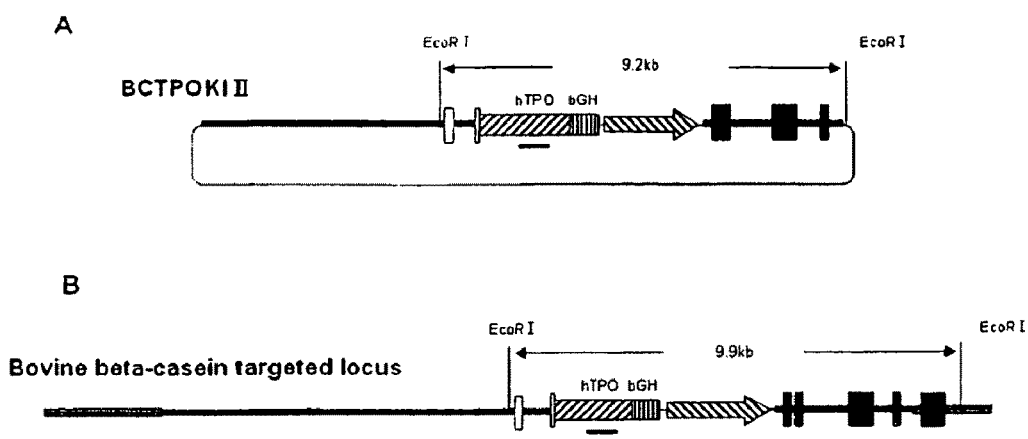
FIG. 30 shows strategy for Southern blot analysis to identify the targeted nucleic acid sequences. The BCTPOKI II vector and purified genomic DNAs from transfected cell clones were digested with EcoRI. The size of DNA fragments from BCTPOKI II vector (A) and genomic DNA (B) digested with the EcoR I restriction enzyme are 9.2 kb and 9.9 kb, respectively. The bar under the hTPO gene represents the locus of the probe used for Southern analysis. 500 bp fragments of hTPO cDNA used for the probe were amplified by PCR.

Two clones identified as gene-targeted by the PCR reactions were analyzed again by the southern blotting. The two cell clones were transferred to two 100 mm culture dishes respectively. Cells were harvested from one of the two dishes, and at least 10 micrograms DNA from each clone was extracted and digested with EcoR 1 for 16 hr at 37° C. EcoR I-digested DNA was separated by electrophoresis through a 0.75% agarose gel at 50V in 1×TAE buffer for 16 hr. The DNA was transferred onto nylon membranes positively charged (Boehringer Mannheim) and hybridized with the probe targeting human TPO cDNA in the vector constructs (see FIG. 30). The probes for southern blotting were prepared with primers of SEQ ID NO 3 and 4 following the guidelines (Roche). The PCR reaction was carried out using "PCR DIG labeling mix" (Roche) and "Taq DNA polymerase" (QIAGEN). Thermal cycling conditions were as below:

| 1 cylcle of | 94° C. | 3 min |
| 30 cycles of | 94° C. | 45 sec |
|  | 52° C. | 30 sec |
|  | 72° C. | 1 min |
| 1 cycle of | 72° C. | 10 min |

Figure 31:
FIG. 31 shows identification of targeted colonies by Southern blot analysis. Two colonies, 81 and 89, were identified to be targeted at the endogenous bovine beta-casein gene locus with the pBCTPOKI II vector of the present invention. The targeted colonies represented the 9.9 kb fragment and the other colonies, 97, 47, 43 and 34, did not show any signal. The bovine genomic DNA was used at the various concentrations as a negative control and the 9.2 kb fragments derived from the pBCTPOKI II vector on various concentrations were used as a positive control.

The gene targeting of the previously identified two clones were confirmed again by the southern blotting (FIG. 31). The two targeted cell clones are number 81 and number 89 cell lines.

The number 81 cell clone was designated as BCTPOK-IbESF81 and deposited with the Korean Collection for Type Cultures (KCTC) located in #52, Oun-dong, Yusong-ku, Taejon 305-333, Republic of Korea on Nov. 10, 2004, under the accession number KCTC-10720BP.

EXAMPLE 7

Preparation of Bovine Somatic Cells

Experiments were conducted according to the Animal Care and Use Committee guidelines of the National Livestock Research Institute of Korea. Bovine embryonic fibroblasts (bEF) were isolated from fetus at Day 45 of gestation of the Holstein cow which produce over 12,000 kg milk a year and prepared as described previously (Koo et al., Biol Reprod., 63(4); 986-992, 2000). The head of the fetus was removed using iris scissors, and soft tissues such as liver and intestine were also discarded by scooping out with two watchmarker's forceps. Bovine ear skin fibroblasts (bESF) were isolated from the ear skin of a 2-years-old Holstein cow which produces over 12,000 kg milk a year. After twice washing with PBS (Gibco BRL), the bEF and bESF were minced with a surgical blade on a 100 mm culture dish. These procedures were performed at room temperature. The minced tissues were incubated in 10 ml of 0.05% (w/v) trypsin/0.53 mM EDTA solution in an incubator at 38.5° C. for 30 min. Trypsin was inactivated by adding an equal volume of cell culture medium supplemented with 10% FBS. The cell culture medium was composed of Dulbecco modified Eagle medium supplemented with 10% FBS, 1000 units of penicillin and 1000 μg/ml of streptomycin (Gibco BRL). After vigorous pipetting, the supernatant was centrifuged at 150×g for 5 min. The cells were suspended and adjusted to a final concentration of $2 \times 10^6$ cells/ml, and then were cultured in 10 ml culture medium at 37° C. in 5% $CO_2$ in air in 175-$cm^2$ tissue culture flasks (Nunc, Roskilde, Denmark) until confluent. The bEF and bESF cells were frozen down in cold Dulbecco's Phosphate-Buffered Saline solution supplemented with 20% FBS and 10% Dimethyl sulphoxide and frozen at −70° C. for 16 hr. The cells were stored in liquid nitrogen until transfection experiment.

To obtain the gene-targeted cell lines, DNA-transfected cells should survive for a long period of culture in vitro without morphological modification and apoptosis. In this invention, BCTPOKI I and BCTPOKI II vectors were introduced into two types of somatic cells: bEF and bESF. It was reported that ovine post-natal fibroblasts persist through longer periods maintaining a relatively stable chromosomal karyotype in culture than in ovine fetal fibroblasts (Williams et al., Mol Reprod Dev., 66(2); 115-125, 2003). In this invention, the bESF sustained much longer normal morphologies in in vitro culture than bEF (Table 2).

TABLE 2

Cell survival rate on passage 4 and passage 8

|  | No. of colonies | | |
| Cell type | P4 | P8 | Survival rate |
|---|---|---|---|
| bEF | 149 | 9 | 6% |
| bESF | 304 | 51 | 17% |

51 (17%) of 304 bESF colonies on passage 4 were expanded by passage 8, showing normal morphologies. However, in case of bEF cells, only 6% clones were cultured by passage 8. In this experiment, we obtained two gene-targeted clones from bESF cells.

EXAMPLE 8

Freezing and Thawing of Frozen Gene-targeted Cells

When the gene-targeted cells were grown to confluent in two 100 mm culture dishes, cells of one plate were subjected to Southern blot analysis. And half of the other plate cells were further expanded and the other half stored in liquid nitrogen after freezing at −70° C. for 16 hr. The procedures of cell sub-culturing and storing were repeated to obtain a lot of cells for use as donor cells. The cell freezing medium consisted of DMEM supplemented with 20% FBS and 10% diethyl sulphoxide (DMSO).

After thawing one vial of frozen gene-targeted cells as soon as possible, the solution was transferred into 15 ml of tube containing 9 ml of cell culture medium and centrifuged 1000 rpm for 3 min. The cell pellet was resuspended in 3 ml culture medium, plated on 6-well culture plate containing 3 ml of culture medium, and then cultured at 37° C. in 5% $CO_2$ in air prior to nuclear transfer.

EXAMPLE 9

Nuclear Transfer

Bovine oocytes obtained from slaughterhouse ovaries were cultured in the maturation medium at 38.57° C. in 5% $CO_2$ in humidified air. The maturation medium consisted of TCM-199 (Sigma Chemical Co.) with Eagle salts and L-glutamine supplemented with 10% (v/v) FBS (Gibco BRL, Grand Island, N.Y.), 1 µg/ml estradiol, 1 µg/ml FSH-P (Schering-Plough Animal Health Corp., Kenilworth, N.J.), and 25 mM $NaHCO_3$. After in vitro maturation, the oocytes were transferred to 500 µl of TL-Hepes supplemented with 0.1% hyaluronidase and then cumulus of the oocytes were removed by mechanical pipetting. The zonae pellucida of denuded oocytes were partially dissected using a fine glass needle (Tsunoda et al., J Exp Zool., 240(1); 119-125, 1986). Oocytes manipulations such as enucleation and cell injection were performed using a micromanipulator equipped with an inverted microscope (Leitz, Ernst Leitz Wetzlar GmbH, Germany). The medium used for manipulation was TL-Hepes containing 7.5 µg/ml cytochalasin B. A first polar body and partial cytoplasm presumptively containing metaphase II chromosomes were removed together by using a micropipette with an inner diameter of 20 µm. Single gene-targeted cells were individually transferred to the perivitelline space of the recipient cytoplast. The cell-cytoplast complexes were equilibrated in a 50 µl drop of cell fusion medium for 10-20 sec and then transferred to a fusion chamber with two electrodes 1 mm apart overlaid with cell fusion medium. The cell fusion medium consisted of 0.3 M mannitol, 0.5 mM Hepes, 0.01% BSA, 0.1 mM $CaCl_2$, and 0.1 mM $MgCl_2$. The cell-cytoplast complexes were induced to fuse with a single pulse of direct current of 1.6 kV/cm for 20 µsec by an Electro Cell Manipulator 2001 (BTX, San Diego, Calif.). These procedures were performed at room temperature. Reconstructed embryos without visible somatic cells were determined as fused eggs 1 h after the fusion pulse. At 4 h after electrofusion, the fused eggs were activated with 5 µM ionomycin for 5 min, followed by treatment with 2.5 mM 6-dimethyl-aminopurine in CR1aa medium (Rosenkrans et al., Biol Reprod., 49(3); 459-462, 1993) supplemented with 10% FBS for 3.5 h at 38.5° C. in 5% $CO_2$ in air.

EXAMPLE 10

Culture of Reconstructed Embryos

The reconstructed embryos were cultured in CR1aa medium supplemented with 1 mM glutamine and 1× Eagle essential amino acids solution (Gibco BRL). After culture for 3 days, cleaved embryos were further cultured in each well of a 4-well culture plate containing 750 µl CR1aa on a mouse embryonic fibroblasts monolayer (with 10% FBS) for 4 days at 38.5° C. in 5% $CO_2$ in air (Park et al., Anim Reprod Sci., 59(1-2); 13-22, 2000). After 7 days of culture, blastocyst formation was observed.

EXAMPLE 11

PCR Analysis of Cloned Embryos

Each embryo was transferred into 20 µl of lysis buffer, which consisted of 50 mM KCl, 1.5 mM $MgCl_2$, 10 mM Tris-HCl pH8.5. 0.5% Nonidet P40, 0.5% Tween and 400 µg/ml Proteinase K, and incubated at 65° C. for 30 min. Proteinase K was inactivated at 95° C. for 10 min (McCreath et al., Nature, 405(6790); 1066-1069, 2000). For the each lysed embryo, the first PCR was carried out with primers of SEQ IN Nos 3 and 4 using the "AccuPower PCR Premix" (Bioneer) and then the nested PCR was performed using 1 µl of the first PCR product. The primers of IN Nos 3 and 7 were used and thermal cycling conditions were as follows:

Nested PCR

SEQ ID No 7
Reverse primer: 5'-gagacggacctgtccagaaagctg-3'

| | | |
|---|---|---|
| 1 cylcle of | 94° C. | 2 min |
| 30 cycles of | 94° C. | 1 min |
| | 65° C. | 30 sec |
| | 72° C. | 45 sec |
| 1 cycle of | 72° C. | 10 min |

It was analyzed by PCR at various different developmental stages whether the cloned embryos were transgenic or not (Table 3).

TABLE 3

PCR analysis of reconstructed embryos at various different developmental stages

| | Developmental stages | | | | | | |
|---|---|---|---|---|---|---|---|
| | 1 cell | 2 cell | 4 cell | 8 cell | 16 cell | morula | blasto-cyst | Total |
| No. of analyzed embryos | 3 | 3 | 6 | 11 | 2 | 3 | 5 | 33 |
| No. of transgenic embryos | 3 | 3 | 6 | 11 | 2 | 3 | 5 | 33 |

As a result, 33 (100%) of 33 cloned embryos were transgenic. The results indicate that the present invention could produce the gene-targeted cloned animals by using the gene-targeted somatic cells.

Figure 32:
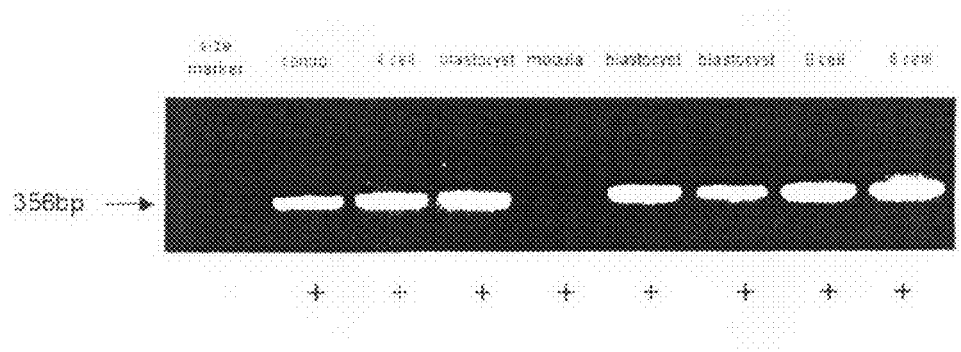
FIG. 32 shows PCR analysis of nuclear-transferred embryos from 81 cell clone. The positive (+) signals, 356 bp in length, implied that the cloned embryos derived from the somatic cells that were targeted with the pBCTPOKI II vector of the present invention. The pBCTPOKI II vector was used as a positive control. And nested PCR was also performed to re-confirm the positive signals.

FIG. 32 shows the PCR analysis result of nuclear-transferred embryos from cell clone 81 (FIG. 23)

EXAMPLE 12

Long-range PCR Analysis of a Fetal Membrane Derived from a Cloned Fetus

Figure 33:
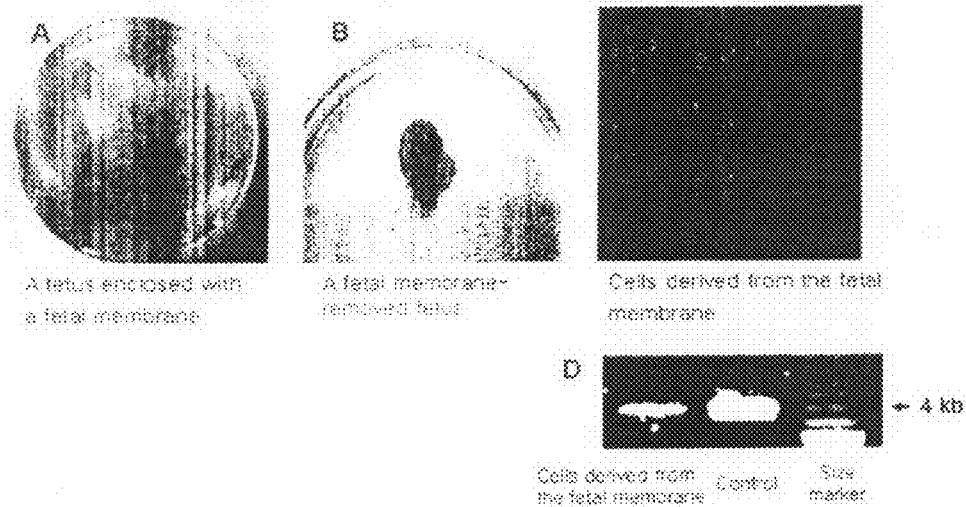
FIG. 33 is a photograph showing a 89 cell clone derived fetus enclosed with a fetal membrane collected at 36 days of gestation (A), the fetal membrane-removed fetus (B) and cells derived from the fetal membrane (C), the result of the long-range PCR of cells derived from the fetal membrane (D). The positive signals for the 4 kb indicate that cells, genetically identical to the cloned fetus, were targeted with the pBCT- POKI II vector of the present invention. The pneoBC3.7 vector was used as a positive control.

Reconstructed embryos at the blastocyst stages were transferred to recipients by a non-surgical method. At 36 days of gestation, a fetus and fetal membrane were flushed from the uterus of the cow non-surgically using a Foley catheter (Agtech, Manhatan, Kans.). The extracted fetus and fetal membrane derived from the fetus were cultured in vitro as described in example 7. The long-range PCR result, showing 4 kb band, confirmed that cultured cells derived from the fetal membrane were accurately targeted into a beta-casein gene in genome with the vector of the present invention (FIG. 33). The procedures of genomic DNA extraction and long-range PCR analysis are the same as described in example 5.

INDUSTRIAL APPLICABILITY

As described herein, the transgenic cattle, which are prepared by implanting a nuclear-transferred embryo introduced with a cell targeted with bovine beta-casein gene targeting vector, can produce a large scale of biomedically or biotechnically valuable proteins in their milk without lethality during embryonic or post-natal developmental stage by unregulated expression of the foreign proteins.

The invention claimed is:

1. A bovine beta-casein gene targeting vector comprising, in operable association, (1) a first nucleic acid region having a length of about 6 kb which comprises the promoter and its flanking nucleic acid sequences of a bovine beta-casein gene, and further comprises exon 1, intron 1, and exon 2 of a bovine beta-casein gene; (2) a region for cloning a nucleic acid coding for desired proteins; (3) a region for coding a positive selection marker; (4) a second nucleic acid region having a length of 2.8 to 3.5 kb which comprises exon 5, 6, 7 and 8, and intron 5, 6 and 7 of bovine beta-casein gene; wherein the nucleic acid segment corresponding to the first region is located upstream to the nucleic acid segment corresponding to the second region in the 5'-3' arrangement of beta-casein gene.

2. The vector according to claim 1, wherein the length of the second region is 3.0 to 3.2 kb.

3. The vector according to claim 1, wherein the positive selection marker is selected from the group consisting of neomycin (Neo), hygromycin (Hyg), histidmol dehydrogenase gene (hisD) and guanine phosphoribosyltransferase (Gpt).

4. The vector according to claim 1, wherein the vector further comprises a region for a negative selection marker.

5. The vector according to claim 4, wherein the negative selection marker is Diphtheria toxin (DT) gene.

6. A method for producing a bovine beta-casein gene-targeted somatic cell which comprises the steps of (1) introducing the bovine beta-casein gene-targeting vector according to claim 1 or 4 into a bovine fibroblast cell;
(2) permitting to occur homologous recombination events in the bovine fibroblast cell; and
(3) selecting the bovine beta-casein gene-targeted bovine embryonic cell or fibroblast cell with a desired gene.

7. The method according to claim 6, wherein the vector in the step (1) is introduced in form of linearized or deleted form lacking plasmid vector backbone.

8. A method for generating transgenic bovine which comprises the steps of (1) introducing the bovine beta- casein gene-targeting vector according to claim 1 or 4 into a bovine fibroblast cell;
(2) permitting to occur homologous recombination events in the bovine fibroblast cell;
(3) selecting the bovine beta-casein gene-targeted fibroblast cell with a desired gene;
(4) introducing the nucleus of the bovine gene-targeted fibroblast cell into a nuclear-removed bovine oocyte to produce a nuclear-transferred bovine embryo;
(5) activating the embryo;
(6) implanting the embryo into a female bovine recipient; and
(7) permitting the implanted embryo to develop.

9. A method for obtaining a large scale of desired proteins which comprise the steps of (1) generating transgenic cattle in accordance with the method of claim 8; (2) inducing lactation in the transgenic bovine; (3) collecting milk from the lactating transgenic bovine; and (4) purifying the desired protein from milk of the transgenic cattle.

* * * * *

```
                              SEQUENCE LISTING

<160> NUMBER OF SEQ ID NOS: 9

<210> SEQ ID NO 1
<211> LENGTH: 31
<212> TYPE: DNA
<213> ORGANISM: Artificial Sequence
<220> FEATURE:
<223> OTHER INFORMATION: primer for bovine casein gene amplification

<400> SEQUENCE: 1
attcagtcga gtggaacata aactttcagc c                                        31

<210> SEQ ID NO 2
<211> LENGTH: 31
<212> TYPE: DNA
<213> ORGANISM: Artificial Sequence
<220> FEATURE:
<223> OTHER INFORMATION: primer for bovine casein gene amplification

<400> SEQUENCE: 2
catatgtcga ctgtgagatt gtattttgac t                                        31

<210> SEQ ID NO 3
<211> LENGTH: 24
<212> TYPE: DNA
<213> ORGANISM: Artificial Sequence
<220> FEATURE:
<223> OTHER INFORMATION: primer for hTPO amplification

<400> SEQUENCE: 3
ggagctgact gaattgctcc tcgt                                                24

<210> SEQ ID NO 4
<211> LENGTH: 24
<212> TYPE: DNA
<213> ORGANISM: Artificial Sequence
<220> FEATURE:
<223> OTHER INFORMATION: primer for hTPO amplification

<400> SEQUENCE: 4
cctgacgcag agggtggacc ctcc                                                24

<210> SEQ ID NO 5
<211> LENGTH: 23
<212> TYPE: DNA
<213> ORGANISM: Artificial Sequence
<220> FEATURE:
<223> OTHER INFORMATION: primer for identification gene targeting

<400> SEQUENCE: 5
ccacacaggc atagagtgtc tgc                                                 23

<210> SEQ ID NO 6
<211> LENGTH: 22
<212> TYPE: DNA
<213> ORGANISM: Artificial Sequence
<220> FEATURE:
<223> OTHER INFORMATION: primer for identification gene targeting

<400> SEQUENCE: 6
ccacagaatt gactgcgact gg                                                  22
```

```
<210> SEQ ID NO 7
<211> LENGTH: 24
<212> TYPE: DNA
<213> ORGANISM: Artificial Sequence
<220> FEATURE:
<223> OTHER INFORMATION: primer for nested PCR

<400> SEQUENCE: 7
gagacggacc tgtccagaaa gctg                                              24

<210> SEQ ID NO 8
<211> LENGTH: 29
<212> TYPE: DNA
<213> ORGANISM: Artificial Sequence
<220> FEATURE:
<223> OTHER INFORMATION: primer for identification gene targeting

<400> SEQUENCE: 8
ttcactgcat tctagttgtg gtttgtcca                                         29

<210> SEQ ID NO 9
<211> LENGTH: 25
<212> TYPE: DNA
<213> ORGANISM: Artificial Sequence
<220> FEATURE:
<223> OTHER INFORMATION: primer for identification gene targeting

<400> SEQUENCE: 9
tctaggacca aacatcggct tactt                                             25
```